United States Patent
Li et al.

(10) Patent No.: US 11,260,386 B2
(45) Date of Patent: Mar. 1, 2022

(54) COMPONENT OF A DEVICE, A DEVICE, AND A METHOD FOR PURIFYING AND TESTING BIOMOLECULES FROM BIOLOGICAL SAMPLES

(71) Applicants: Yongmei Li, Kinnelon, NJ (US); Li Li, Kinnelon, NJ (US)

(72) Inventors: Yongmei Li, Kinnelon, NJ (US); Li Li, Kinnelon, NJ (US)

(73) Assignee: THE EMERTHER COMPANY, Shanghai (CN)

( * ) Notice: Subject to any disclaimer, the term of this patent is extended or adjusted under 35 U.S.C. 154(b) by 531 days.

(21) Appl. No.: 14/732,423

(22) Filed: Jun. 5, 2015

(65) Prior Publication Data
US 2016/0354773 A1    Dec. 8, 2016

(51) Int. Cl.
*B01L 3/00*        (2006.01)
*G01N 1/34*        (2006.01)
(Continued)

(52) U.S. Cl.
CPC ............. *B01L 3/502* (2013.01); *B01L 3/508* (2013.01); *B01L 3/52* (2013.01); *B01L 3/561* (2013.01); *B01L 3/565* (2013.01); *C12Q 1/6806* (2013.01); *G01N 1/34* (2013.01); *G01N 1/405* (2013.01); *B01L 2200/028* (2013.01); *B01L 2200/0647* (2013.01); *B01L 2200/085* (2013.01); *B01L 2300/044* (2013.01);
(Continued)

(58) Field of Classification Search
CPC .. B01L 3/502; B01L 3/508; B01L 3/52; B01L 3/561; B01L 3/565; B01L 2300/0672; B01L 2300/087; B01L 2200/0647; B01L 2400/06; B01L 2200/028; B01L 2400/0481; B01L 2200/085; B01L 2300/044; B01L 2300/0636; B01L 2300/12; B01L 2400/043; G01N 1/34; G01N 1/38; G01N 35/0098; C12Q 1/6806
See application file for complete search history.

(56) References Cited

U.S. PATENT DOCUMENTS 5,176,203 A    1/1993 Larzul
5,656,501 A    8/1997 Yedgar et al.
(Continued)

FOREIGN PATENT DOCUMENTS

CN    101149376 A    3/2008
CN    101945705 A    1/2011
(Continued)

OTHER PUBLICATIONS

Kwon et al. Development of a Self-contained Sample Preparation Cartridge for Automated PCR Testing. Biochip Journal 2015; 9(4): 300-305 (Year: 2015).*
(Continued)

*Primary Examiner* — Angela M. Bertagna
(74) *Attorney, Agent, or Firm* — Liang & Hennessey LLP; Stanley D. Liang

(57) ABSTRACT

The present disclosure relates to, inter alia, an easy-to-operate, fully closed component, which can be part of an instrument, for purification of biomolecules from biological samples, and subsequent transfer, and testing of the biomolecules, as well as an instrument comprising the component, and a method for using the component.

11 Claims, 29 Drawing Sheets

(51) Int. Cl.
  *G01N 1/40* (2006.01)
  *G01N 1/38* (2006.01)
  *C12Q 1/6806* (2018.01)
  *G01N 35/00* (2006.01)

(52) U.S. Cl.
  CPC .......... *B01L 2300/0636* (2013.01); *B01L 2300/0672* (2013.01); *B01L 2300/087* (2013.01); *B01L 2300/12* (2013.01); *B01L 2400/043* (2013.01); *B01L 2400/0481* (2013.01); *B01L 2400/06* (2013.01); *G01N 1/38* (2013.01); *G01N 35/0098* (2013.01)

(56) References Cited

U.S. PATENT DOCUMENTS

| | | | |
|---|---|---|---|
| 5,912,129 A * | 6/1999 | Vinayagamoorthy | B01L 7/52 435/6.12 |
| 6,318,191 B1 | 11/2001 | Chen | |
| 6,748,332 B2 | 6/2004 | Chen | |
| 6,780,617 B2 | 8/2004 | Chen | |
| 6,964,862 B2 | 11/2005 | Chen | |
| 7,337,072 B2 | 2/2008 | Chen | |
| 7,718,421 B2 * | 5/2010 | Chen | B01L 3/502 206/219 |
| 7,727,473 B2 * | 6/2010 | Ching | B01F 11/0071 422/610 |
| 7,785,535 B2 | 8/2010 | Chen et al. | |
| 7,799,521 B2 | 9/2010 | Chen | |
| 7,833,489 B2 | 11/2010 | Chen | |
| 7,935,504 B2 | 5/2011 | Chen | |
| 8,148,116 B2 | 4/2012 | Chen | |
| 8,394,642 B2 | 3/2013 | Jovanovich et al. | |
| 8,414,845 B2 | 4/2013 | Chen et al. | |
| 8,598,338 B2 | 12/2013 | Bair et al. | |
| 8,802,038 B2 | 8/2014 | Wilkinson et al. | |
| 8,936,933 B2 | 1/2015 | Chen et al. | |
| 2002/0049557 A1 | 4/2002 | Chen | |
| 2002/0086417 A1 | 7/2002 | Chen | |
| 2003/0049833 A1 | 3/2003 | Chen et al. | |
| 2004/0105782 A1 | 6/2004 | Chen | |
| 2004/0125704 A1 | 7/2004 | Ishi et al. | |
| 2004/0161788 A1 | 8/2004 | Chen et al. | |
| 2004/0223878 A1 | 11/2004 | Chen | |
| 2005/0019875 A1 | 1/2005 | Chen | |
| 2005/0032105 A1 | 2/2005 | Bair et al. | |
| 2006/0154341 A1 | 7/2006 | Chen | |
| 2007/0292858 A1 | 12/2007 | Chen et al. | |
| 2008/0003564 A1 | 1/2008 | Chen et al. | |
| 2008/0038813 A1 | 2/2008 | Chen | |
| 2008/0125704 A1 | 5/2008 | Anderson | |
| 2008/0145275 A1 | 6/2008 | Chen | |
| 2010/0160619 A1 | 6/2010 | Bair et al. | |
| 2010/0218621 A1 | 9/2010 | Chen et al. | |
| 2010/0323919 A1 | 12/2010 | Chen et al. | |
| 2011/0064613 A1 | 3/2011 | Chen | |
| 2011/0143968 A1 | 6/2011 | Chen et al. | |
| 2011/0207121 A1 | 8/2011 | Chen | |
| 2011/0236960 A1 | 9/2011 | Bird et al. | |
| 2012/0276532 A1 | 11/2012 | Chen | |
| 2013/0040830 A1 | 2/2013 | Chen | |
| 2014/0272937 A1 | 9/2014 | Haselton et al. | |
| 2014/0272965 A1 | 9/2014 | Handique et al. | |

FOREIGN PATENT DOCUMENTS

| | | |
|---|---|---|
| EP | 2334433 A1 | 6/2011 |
| JP | 2008298692 A | 12/2008 |
| JP | 2009512447 A | 3/2009 |
| JP | 2011508203 A | 3/2011 |
| JP | 2012504487 A | 2/2012 |
| WO | 9967647 A1 | 12/1999 |
| WO | 0113127 A1 | 2/2001 |
| WO | 2006028616 A1 | 3/2006 |

OTHER PUBLICATIONS

Japanese Application No. 2018-515189, Office Action dated Jul. 30, 2019, 6 pages.

* cited by examiner

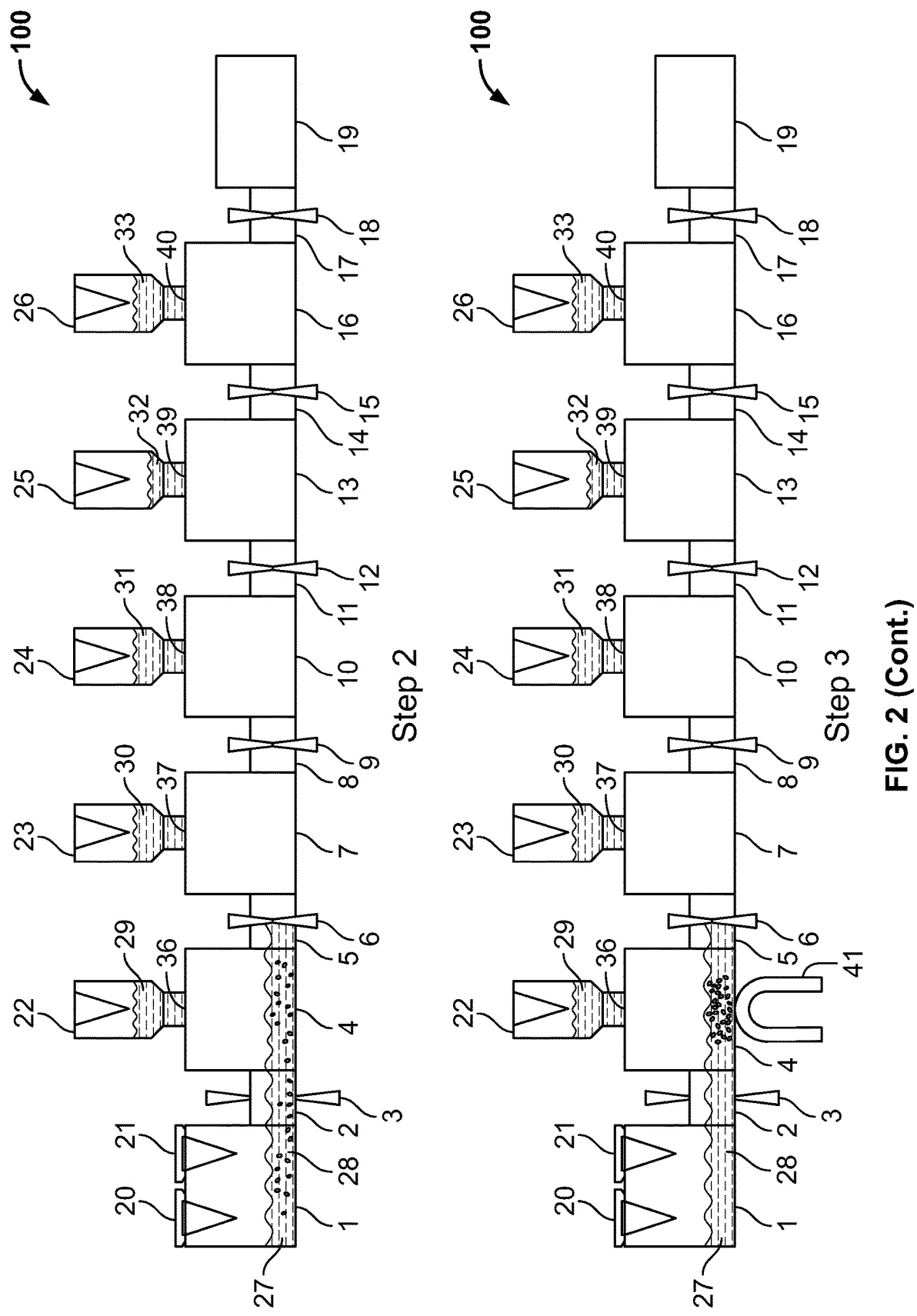

Step 4

Step 5

Step 7

Step 8

Step 9

Step 10

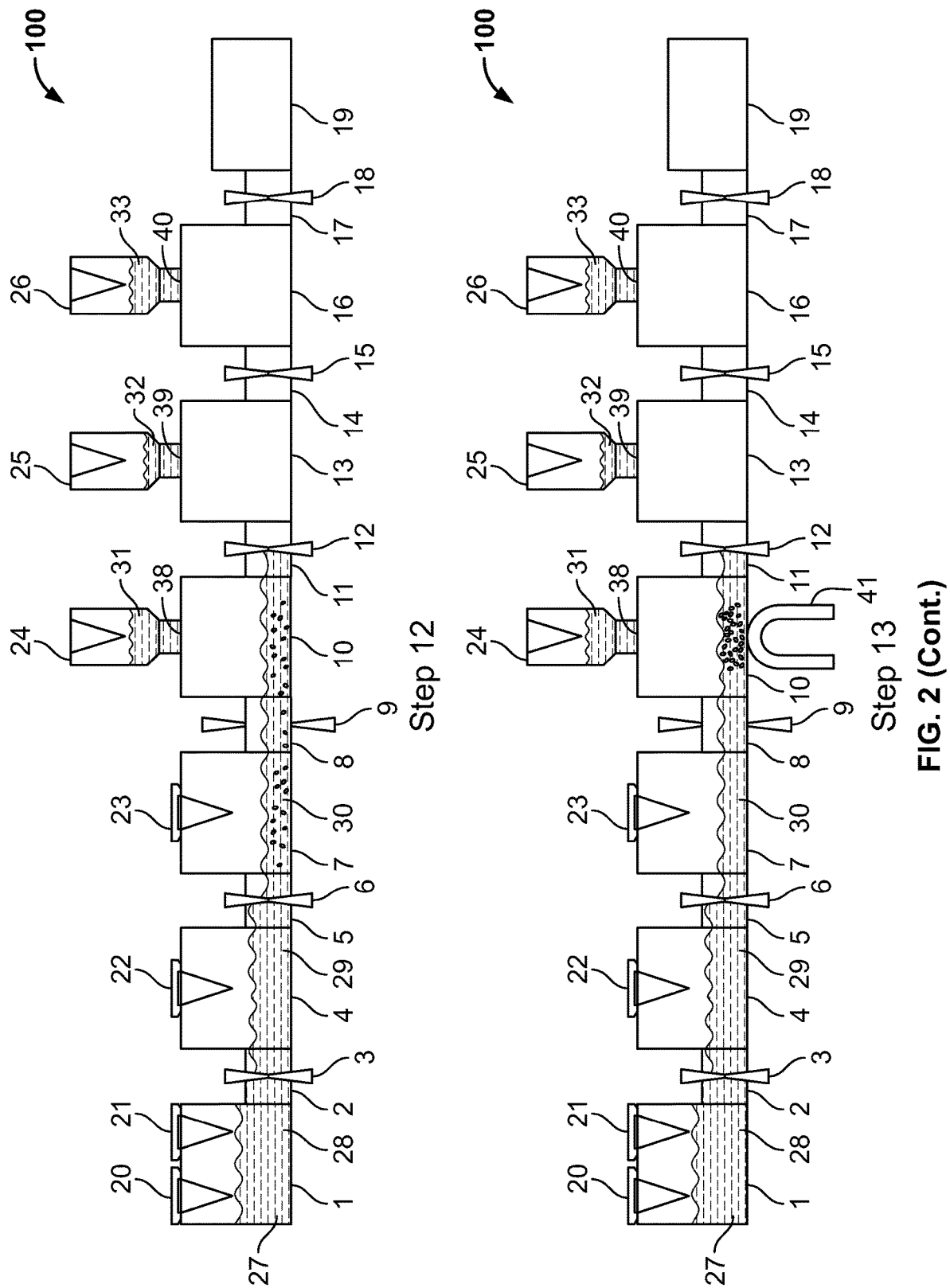

Step 14

Step 15

Step 16

Step 19

Step 20

Step 23

Step 24

Step 25

Step 26

COMPONENT OF A DEVICE, A DEVICE, AND A METHOD FOR PURIFYING AND TESTING BIOMOLECULES FROM BIOLOGICAL SAMPLES

TECHNICAL FIELD OF THE INVENTION

The present invention relates to the field of medical devices relating to purifying biomolecules from a biological sample and testing the biomolecules.

BACKGROUND

Biological samples include blood, saliva, oral mucosa, body fluids, hair roots, feces, and tissues. Extraction and purification of biomolecules, including nucleic acids, proteins, and small molecules, from biological samples are required for many medical applications, such as for diagnostics. Typically, blood or other biological samples are collected and sent to a central laboratory for separation and extraction (i.e., purification) of nucleic acids, proteins, or small molecules, followed by analysis and/or testing. Because these biological samples potentially contain infectious viruses and bacteria, they are a health risk for the operators. In addition, some purification and detection reagents may adversely impact laboratory environment and/or the health of the operating personnel. Therefore, a fully closed purification and testing system for biological samples can effectively prevent continuous exposure of the operating personnel to the source of infection and harmful chemicals, reduce cross-contamination between samples, and improve the diagnostic accuracy. In addition, an easy-to-operate and small-sized instrument also provides convenience for point-of-care diagnosis, and testing in individual labs and field.

There is a need for a fully closed, easy-to-operate component of a device (i.e., an instrument or a machine) that can achieve functions including liquid addition, solid-liquid mixing, magnetic separation, and sample transfer.

SUMMARY OF THE INVENTION

This invention solves the problem discussed above, by providing, in one aspect, a fully-closed, easy-to-operate component (i.e., a unit), which can be part of a device (i.e., an instrument or a machine), or not, for use for purifying biomolecules from biological samples; and testing (including analyzing) or storing these biomolecules can be performed in the same component. The component and the instrument comprising the component have functions including liquid addition, solid-liquid mixing, magnetic separation, and sample transfer, and can be used for purification, transfer, and testing of biomolecules. The fully closed, easy-to-operate component comprises: mixing chambers, connection tubes (also referred to herein as connecting tubes), storage containers, sealing membranes, pressure seals or switches, purified sample collection tubes or testing chambers, sample (a biological sample in solution, suspension or solid form), magnetic beads, lysis/binding buffer (comprising lysis buffer and/or binding buffer), washing solution, optionally eluent, optionally test solution, optionally a sample collection device with a sealing cap, and optionally a detection sensor.

In another aspect, an instrument comprising this component is provided. The instrument also comprises a moving magnetic field, a motor, and means for rotating, vibrating, and tilting the component. However, the component can function manually without the machine.

In yet another aspect, a method is provided of purifying biomolecules from a biological sample and testing or storing the purified biomolecules using the component of the instrument of this invention, with or without the instrument.

Numerous other aspects are provided in accordance with these and other aspects of the invention. Other features and aspects of the present invention will become more fully apparent from the following detailed description and the appended claims.

DETAILED DESCRIPTION OF THE INVENTION

Figure 1:
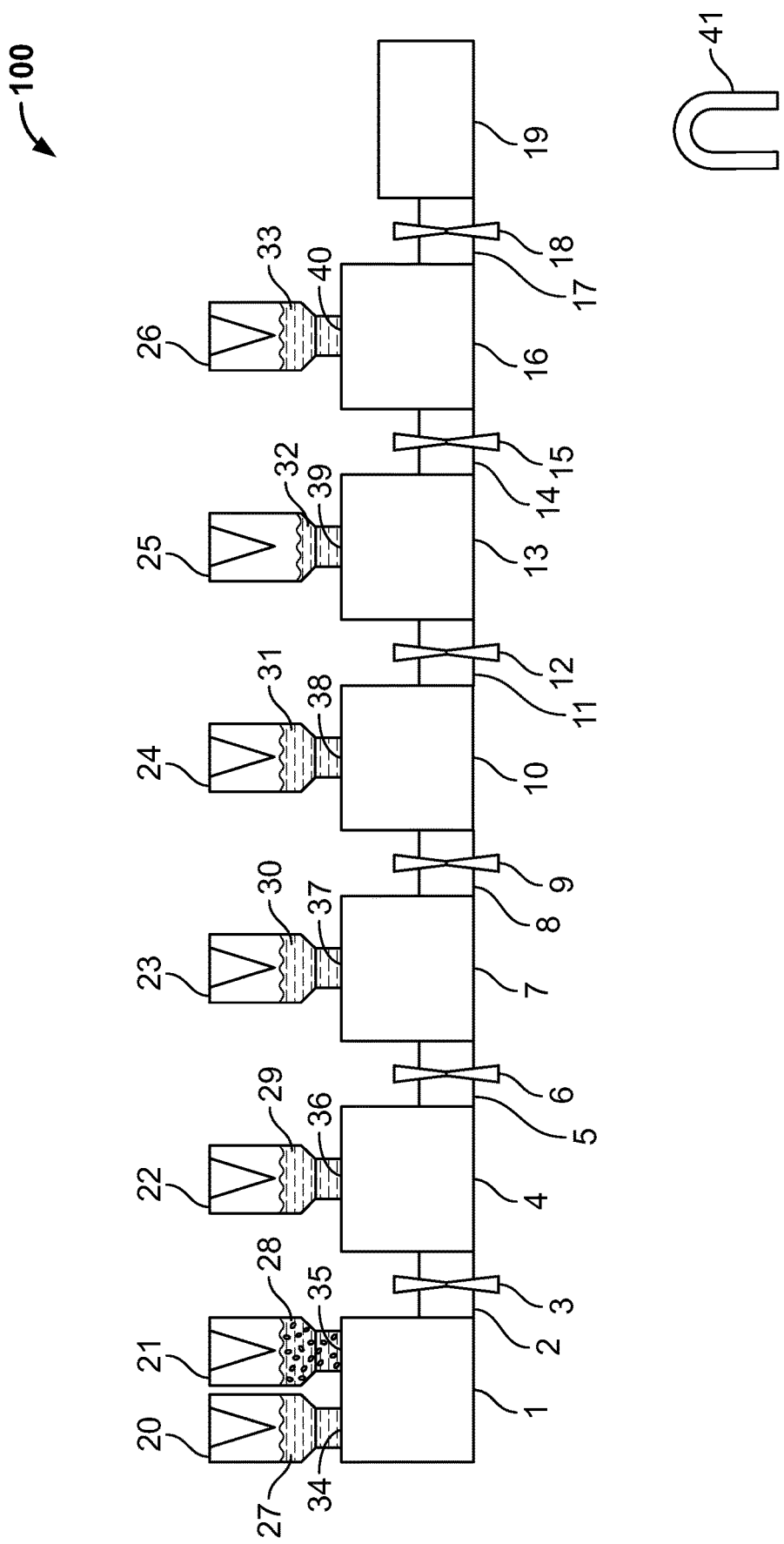
FIG. 1 depicts embodiments of the component of the instrument of this invention and a magnetic field.

The component of this invention, which can be part of a machine, or not, is used for extraction and purification of biomolecules, such as nucleic acids, proteins, or small molecules, from a variety of biological samples. Testing solution and detection sensor are not needed for this application. After obtaining the purified biomolecules, the biomolecules can be stored stably. Therefore, it is especially suitable for large-scale biological sample collection and storage, such as sample collection in common laboratories or in the field, and the like. With the addition of test solution and a detection sensor, the component of the instrument can also be used for testing for laboratory and medical use, including but not limited to point-of-care diagnostic testing (such as diagnosis of infectious diseases, cancer, and other diseases as well as genotyping), gene sequencing, quantitation of biomolecules, and other suitable applications.

In one aspect, this invention provides a fully closed (i.e., sealed) component, which can be part of an instrument (a device or a machine), or not. The component provides a system for purifying, and possibly further testing (including analyzing), a biomolecule from a biological sample. The component comprises: mixing chambers, connection tubes, storage containers, sealing membranes, pressure seals or switches, purified sample collection tubes or testing chambers, sample (a biological sample in solution, suspension or solid form), magnetic beads, lysis/binding buffer (comprising lysis buffer and/or binding buffer), washing solution, optionally eluent, optionally test solution, optionally a sample collection device with a sealing cap, and optionally detection sensor(s), used for testing. The detection sensor varies depending on the test performed and any detector device is contemplated. The detector device may or may not be part of the component and may or may not be part of the machine. Any part of the component can be made of any suitable material and can be of any suitable size. Any part of the component can be made by any suitable means known in the art, such as by extrusion, injection molding, blow molding, and 3-D printing. The parts of the component can be connected by methods known in the art. In certain embodiments, the component is made of plastic. Any kind of plastic is contemplated, such as polyvinylchloride. In certain embodiments, the component is approximately the size of a ball point pen. In certain embodiments, the component can be sterilized prior to use by methods known in the art.

In another aspect, an instrument (i.e., a device or a machine) is provided. The instrument is adapted to house the component of this invention. The instrument can also comprises a moving magnetic field, means to move the magnetic field, a motor, means for rotating, vibrating, and tilting the component, electrical plug, electrical components, motor, and other components necessary for its function. The instrument is adapted to be linked to a power supply (AC and/or DC). The instrument can comprise a detection sensor. In certain embodiments, the instrument comprises a computer processor, which optionally comprises a computer readable medium, such as a DVD, CD, memory stick. In certain embodiments, the instrument comprises a heater/cooler, or is linked to a heater/cooler. Any suitable heater/cooler is contemplated. The machine can comprise suitable mounting means and transport means, such as conveyer track or robotic arms. Any suitable machines are contemplated and can be made by conventional methods using any suitable materials and be of any suitable size.

In certain embodiments, the instrument is connected to a computer, which has a processor, and the computer optionally comprises a computer readable medium. The computer readable medium can be part of a computer device, with a processor that can process the medium. The computer can be used to process and store the data, such as those generated from testing the biomolecules, and optionally to operate the machine. The computer can be any computer, including laptops, tablets, phones, mainframe computers, and desktop computers.

A "computer readable medium" refers to a medium capable of storing data in a format readable by a computer or a computer-related mechanical device. Examples of such computer readable media include magnetic media such as magnetic disks, cards, tapes, drums, punched cards and paper tapes, optical disks (e.g., CD, CD-ROM, CD-R, CD-RW, DVD, etc.), on-line data storage/transfer, and other media well known in the art. The medium can be used, for example, to store test data.

With the instrument, all or part of the applications can be done in an automated fashion. The component can also be operated manually, in the absence of an instrument, but in the presence of a magnetic field. The machine can also be operated, at least in part, manually by an operator.

These and other embodiments of the invention are described below with reference to FIGS. 1-5 wherein like numerals are used throughout to denote like elements.

FIG. 1 depicts embodiments of a component 100 of this invention. The component can be made of any suitable material. Such as, for example, plastic. The component can be any suitable size, such as the size of a ball point pen. A magnetic field is also shown. Both the component and the magnetic field can be part of a machine, or not.

1. A plurality of mixing chambers 1, 4, 7, 10, 13, and 16. There can be more mixing chambers or fewer mixing chambers. The mixing chambers are located in a row horizontally and adjacently. The mixing chambers could also be located in other suitable manner, such as vertically and adjacently. In certain embodiments, the mixing chambers are disposable plastic containers.

2. A plurality of connection tubes 2, 5, 8, 11, 14, and 17. There can be more connection tubes or fewer connection tubes. Each connection tube connects two adjacent mixing chambers or a mixing chamber and a purified sample collection tube or testing chamber. In certain embodiments, the connection tube is a sealable soft tube. In other embodiments, the connection tube is a switch. Any suitable tube or any suitable switch is contemplated. The tube or switch can be of any suitable size and made by any suitable means known in the art.

3. A plurality of storage containers 20, 21, 22, 23, 24, 25, and 26. There can be more storage containers or fewer storage containers. In certain embodiments, a storage container is compressible. One or more of the storage containers is mounted above each mixing chamber. Each storage container is in direct physical contact with the mixing chamber below it, but not in direct fluid contact. When there are more than one storage containers mounted on a mixing chamber, they can be located next to each other. The storage containers could also be located in other suitable locations. Each storage container comprises a puncture device. One or more storage containers comprise magnetic beads. The magnetic beads are for adsorption and binding of small molecule, protein and/or nucleic acids (such as DNA and/or RNA). In certain embodiments, each of three or more storage containers comprise a different type of magnetic beads, one for purifying nucleic acids, one for purifying proteins, and one for purifying small molecules. Suitable lysis/binding buffer (buffer that can lyse cells [lysis buffer] and/or enhance binding of the biomolecules to the magnetic beads [binding buffer]) are provided. Nucleic acids, proteins, and small molecules are known in the art; different magnetic beads for purifying them are also well known in the art. In certain embodiments, a storage container can comprise one or more of: lysis/binding buffer, a buffer that can lyse cells and/or enhance binding of the biomolecules to the magnetic beads; washing solution, a solution for removing impurities non-specifically bound to magnetic beads; eluent, a solution for eluting biomolecules from the magnetic beads; test solution/dry powder, for qualitative or quantitative analysis of the purified biomolecules. In certain embodiments, the lysis/binding buffer comprises both lysis buffer and binding buffer and can be stored in one storage container. In certain embodiments, the lysis/binding buffer can be separated buffers, which are stored in different storage containers, or only one buffer (lysis buffer or binding buffer) is used. In certain embodiments, the magnetic beads and the lysis/binding buffer are stored in different storage containers. In certain other embodiments, the magnetic beads and the lysis/binding buffer are stored in the same storage container. In certain embodiments, the storage container is a disposable container. In certain further embodiments, the storage container is a compressible disposable container. In certain embodiments, the storage container is a plastic container preloaded with a certain quantity of liquid, solid, or solid-liquid suspension. In certain embodiments, the volume of the storage container is about 0.01 ml to about 15 ml. The storage container can be made by any suitable materials and method and can be of any suitable size holding any suitable volume. Storage containers can be stored at different places (for example, locations with different temperature), and attached to mixing chambers or testing chambers prior to operation.

4. A plurality of sealing membranes 34, 35, 36, 37, 38, 39, and 40. There can be more sealing membranes or fewer sealing membranes. A mixing chamber is connected with one or more storage containers, with a sealing membrane between the connected mixing chambers and storage containers. The biological sample enters the component system through the use of the sealing membrane 34. The sample can also enter from other sealing membranes rather than just one sealing membrane and/or from a storage container. In certain embodiments, a syringe or a pipette is used to add the sample into storage container 20 or directly to the mixing chamber 1 using a sealing membrane. A sealing membrane is a piercible membrane, piercible by syringe, pipette, capillary, or by pressure. In certain embodiments, the sealing membrane of the storage container is sealed foil, plastic or rubber closure. The sealing membrane of the storage container prevents the transfer of the liquid, solid, or solid-liquid suspension to the mixing chamber before the membrane is pierced, thus preventing the storage container and the mixing chamber to be in fluid contact until the membrane is pierced. The structural integrity of the sealing membrane can be damaged by the piercing device via compression, causing the liquid, solid, or solid-liquid suspension to move from a storage chamber into a mixing chamber.

5. A plurality of pressure seals 3, 6, 9, 12, 15, and 18. There can be more pressure seals or fewer pressure seals. Each pressure seal is located in between adjacent mixing chambers or a mixing chamber and a purified sample collection tube/testing chamber on a connection tube. The pressure seals are adapted for opening and/or closing the connection tube, to enable and/or disable the liquid exchange between adjacent mixing chambers or a mixing chamber and a purified sample collection tube/testing chamber. The pressure seals can be made of any suitable materials and method and can be of any suitable size. A switch can be used instead of a pressure seal.

6. A purified sample collection tube or testing chamber 19. The purified sample collection tube or testing chamber 19 is located adjacent to the last mixing chamber (16). A purified sample collection tube or testing chamber can be located in any suitable location, such as below or above a mixing chamber, and there can be any suitable numbers of sample collection tube/testing chamber. In certain embodiments, one or more of the mixing chambers are connected with one or more testing chambers or one or more purified sample collection tubes such that the biomolecules purified from a biological sample is transferred from the mixing chamber to the testing chambers for testing or to the sample collection tubes for collection. In certain embodiments, there is a one-way membrane between the connected mixing chambers and testing chambers or purified sample collection tubes such that the biological sample is allowed to flow from the mixing chamber into the testing chamber or purified sample collection tubes, but not back to the mixing chamber. In certain embodiments, the mixing chambers and testing chambers or purified sample collection tubes are connected using a connection tube, which is a sealable soft tube. In certain embodiments, the mixing chambers and testing chambers or purified sample collection tubes are connected using a switch. The purified sample collection tube or testing chamber can be made of any suitable materials and method and can be of any suitable size.

7. Sample solution 27, placed in the storage container 20. The sample solution comprises the biological sample and can further comprise other suitable ingredients, such as for example, PMSF, salts, buffer, saline, anticoagulant, etc.

8. Magnetic beads and lysis/binding buffer (comprising lysis buffer and/or binding buffer) 28: placed in the storage container 21. Magnetic beads and lysis/binding buffer can also be placed in separate storage containers.

The lysis/binding buffers can be commercially available, such as those from, for example, The Emerther Company, Shanghai, China, ThermoFisher Scientific, Waltham, Mass., and Beckman Coulter, Jersey City, N.J. The lysis/binding buffer is any suitable buffer for the magnetic beads, and can be lysis-binding buffer for lysing the cells and/or enhancing binding of certain biomolecules to the magnetic beads. Depending on the application (i.e., purifying different biomolecules), a person skilled in the art would know to use different lysis/binding buffer and magnetic beads. For example, the lysis/binding buffer can be a single solution comprising the following components: chaotropic salt, at a concentration of 3-6M; salt, at a concentration of 0.01-3M, wherein the salt comprises monovalent salts, such as alkali metal salts and ammonium salts, divalent salts, such as magnesium salts and zinc salts, or combinations thereof; a surfactant, at a concentration of 2-5% (v/v); and alcohol, at a concentration of 20-50% (v/v), wherein said alcohol is ethanol or isopropanol. This lysis/binding buffer can further comprise chelating agent at a concentration of 0-100 mM, preferably 0.5 mM-100 mM. The lysis/binding buffer can also be 4M guanidine hydrochloride, 2% Triton™ X-100 (t-octylphenoxypolyoxyethanol), 0.1% SDS, 0.01% mercaptoethanol, 0.1M NaCl, 0.6M LiCl, 10 mM Tris-HCl (pH5.5), 1 mM EDTA, 25% isopropanol.

Magnetic beads are used to purify biomolecules, including nucleic acids, proteins, and small molecules, through adsorption via a magnetic field. Under the right conditions, the biomolecules bind to the magnetic beads in a magnetic field and the materials that cannot bind remain in solution and can be removed. The bound biomolecules can then be eluted off of the magnetic beads in appropriate buffer and separated from the magnetic beads using the magnetic field. Any appropriate magnetic beads (also referred to as magnetic particles, magnetic microparticles, or magnetic nanoparticles) can be used. Examples include, without limitation, commercially available silanol silica magnetic microparticles, aminated silica magnetic microparticles, and carboxylated silica magnetic microparticles. Magnetic beads have been used in separation and detection of biological sample, nucleic acid extraction, immunoassay, etc.

9. Washing solution 29, 30, and 31, placed in storage containers 22, 23, and 24, respectively.

The washing solution can be commercially available, such as those from, for example, The Emerther Company, Shanghai, China, ThermoFisher Scientific, Waltham, Mass., and Beckman Coulter, Jersey City, N.J. The washing solution is any suitable washing solution. The washing solution can comprise, for example, detergents, etc. For example, the washing solution can comprise 200 mM NaCl solution, 0.8M LiCl, 70% ethanol, 50 mM Tris buffer (pH6.5). Or, for another example, the washing solution can comprise 70% to 75% ethanol.

10. Eluent 32, placed in a storage container 25. The eluent comprises buffers to elute the purified biomolecules from the magnetic beads. For certain embodiments, eluent is optional.

The eluent can be commercially available, such as those from, for example, The Emerther Company, Shanghai, China, ThermoFisher Scientific, Waltham, Mass., and Beckman Coulter, Jersey City, N.J. The eluent is any suitable eluent. For example, the eluent can be 1 mM EDTA, 10 mM Tris-HCl (pH8.0), TE buffer pH7.5-8.5, or sterile water.

11. Test solution 33, placed in a storage container 26, which is attached to a mixing chamber. In certain embodiments, test solutions can also be stored in storage containers which are attached to a testing chamber, so the test solutions can be directly added to the testing chamber.

The skilled artisan would appreciate that the test solution differs depending on the test performed and can be commercially available, such as those from, for example, ThermoFisher Scientific, Waltham, Mass., and Beckman Coulter, Jersey City, N.J. The test solution is any suitable test solution and can also be a dry powder.

12. A moving magnetic field 41 can be placed at the mixing chamber 1, 4, 7, 10, 13, or 16 or at the purified sample collection tube or testing chamber 19, or located in positions where the magnetic field does not affect the seal units. In certain embodiments, the moving magnetic field is part of the instrument and not part of the sealed component. The position of the magnetic field can be changed, thus adsorbing the magnetic beads and allowing the magnetic beads to be suspended or attracted and enriched in the mixing chambers.

The component is fully sealed (a completely closed system) and there is no material exchange between the sealed component and open external environment (e.g., liquid, gas, including water, oxygen and other substances of diffusion, etc.).

Figure 2:
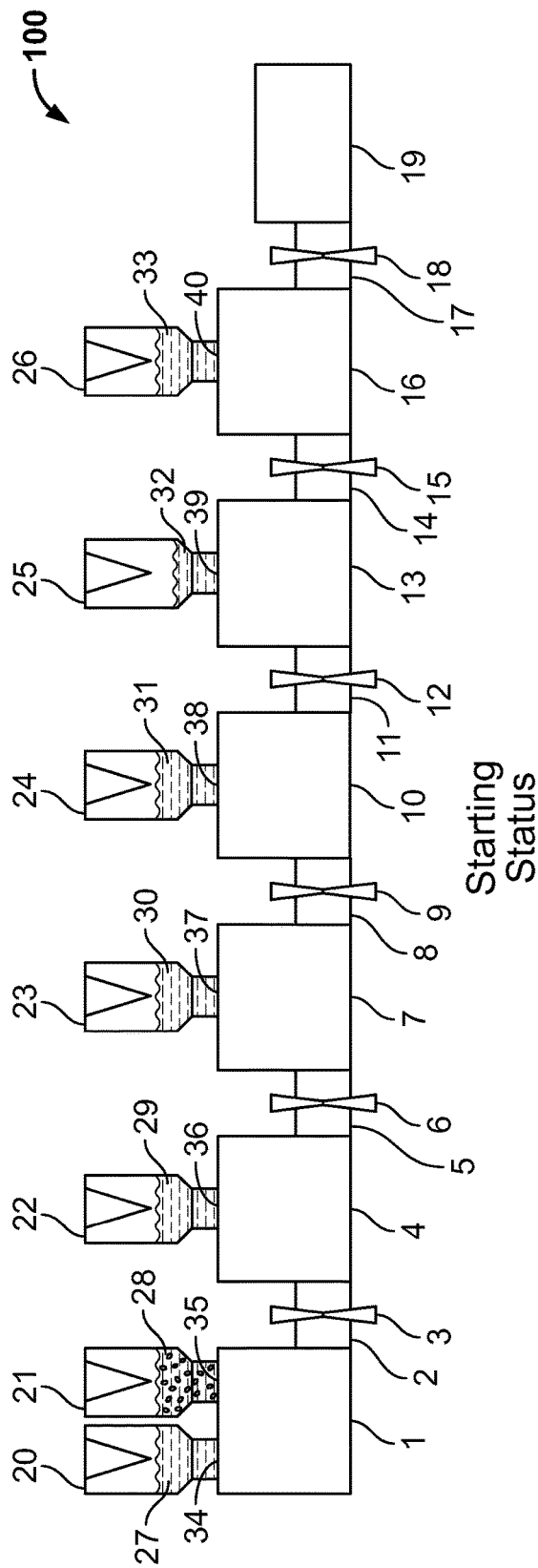
FIG. 2 depicts performing an exemplary extraction and detection process using embodiments of the component of the instrument of this invention and a magnetic field, according to embodiments of the present invention.
Figure 2:
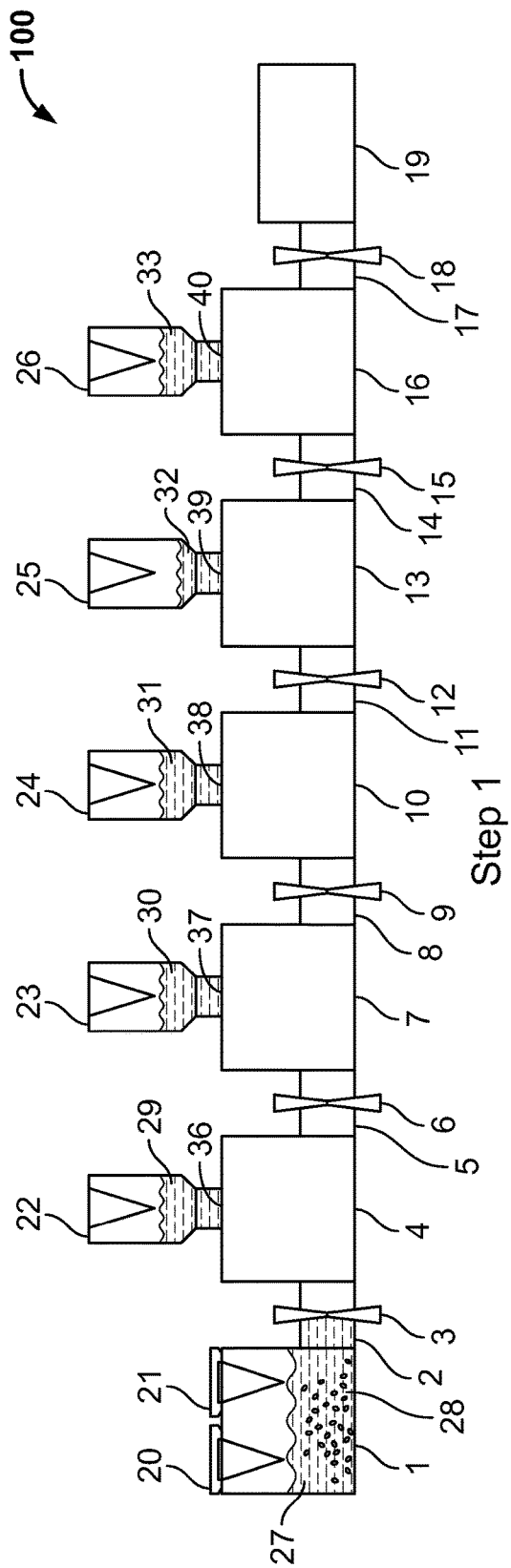
Figure 2:
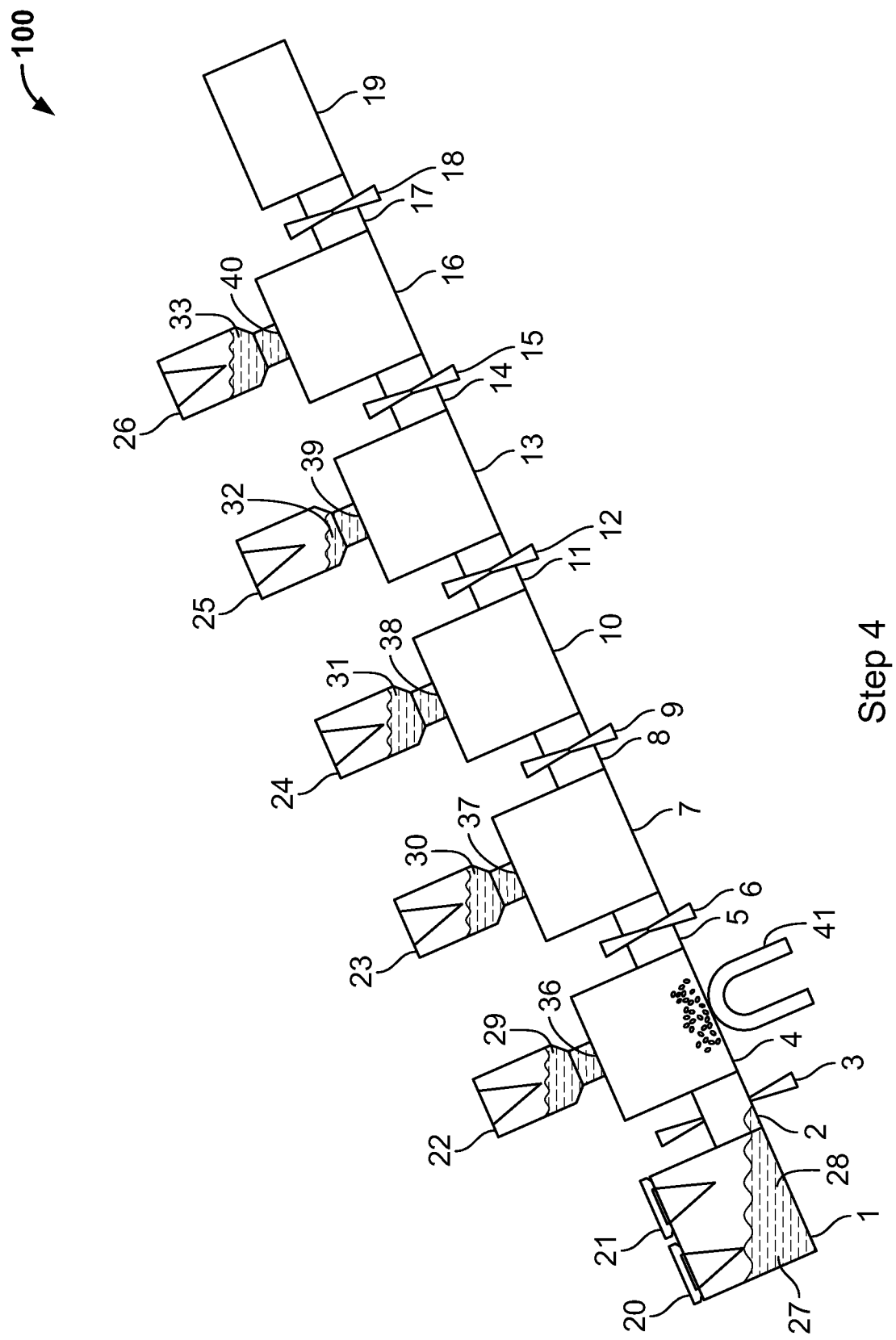
Figure 2:
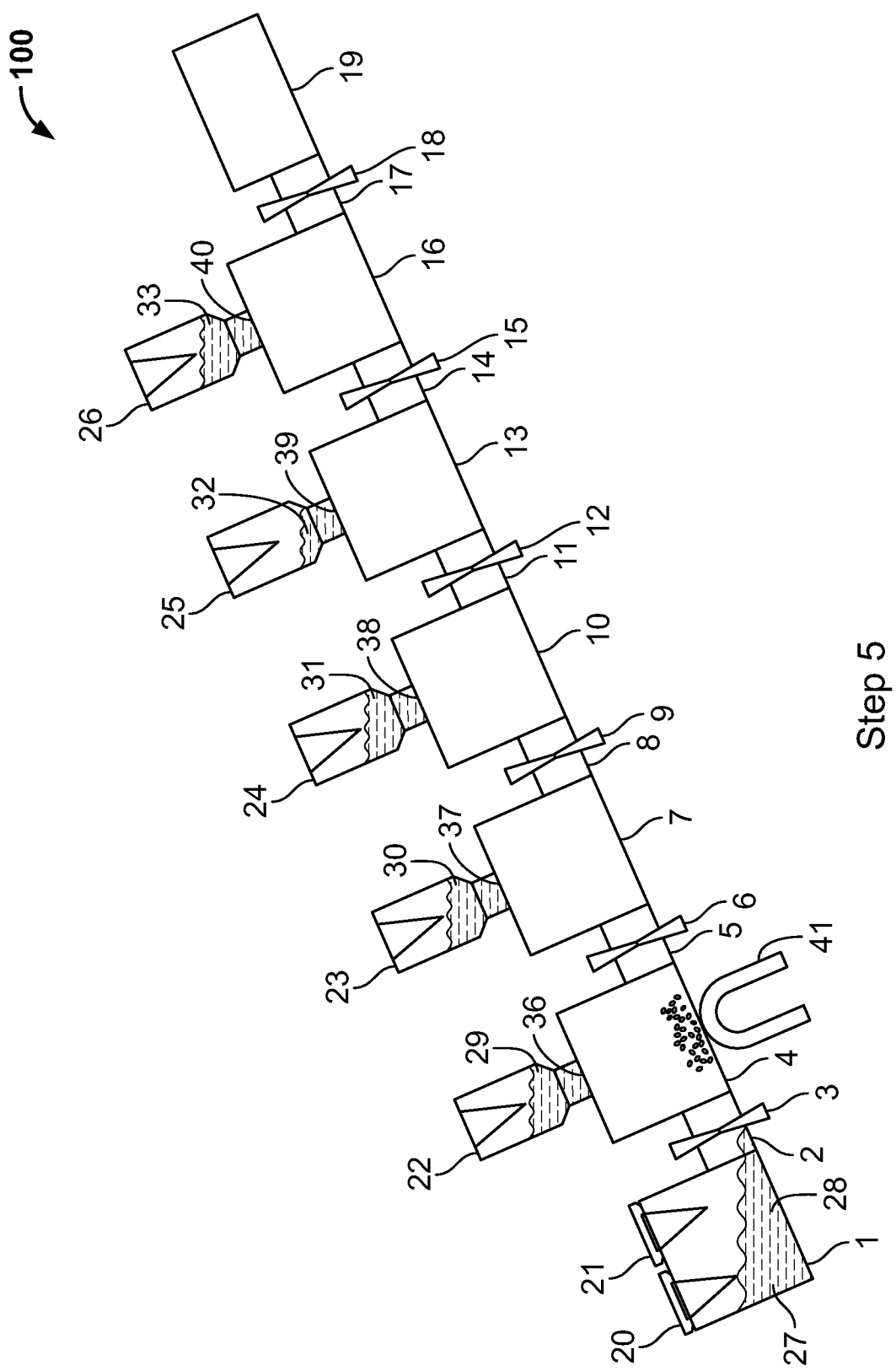
Figure 2:
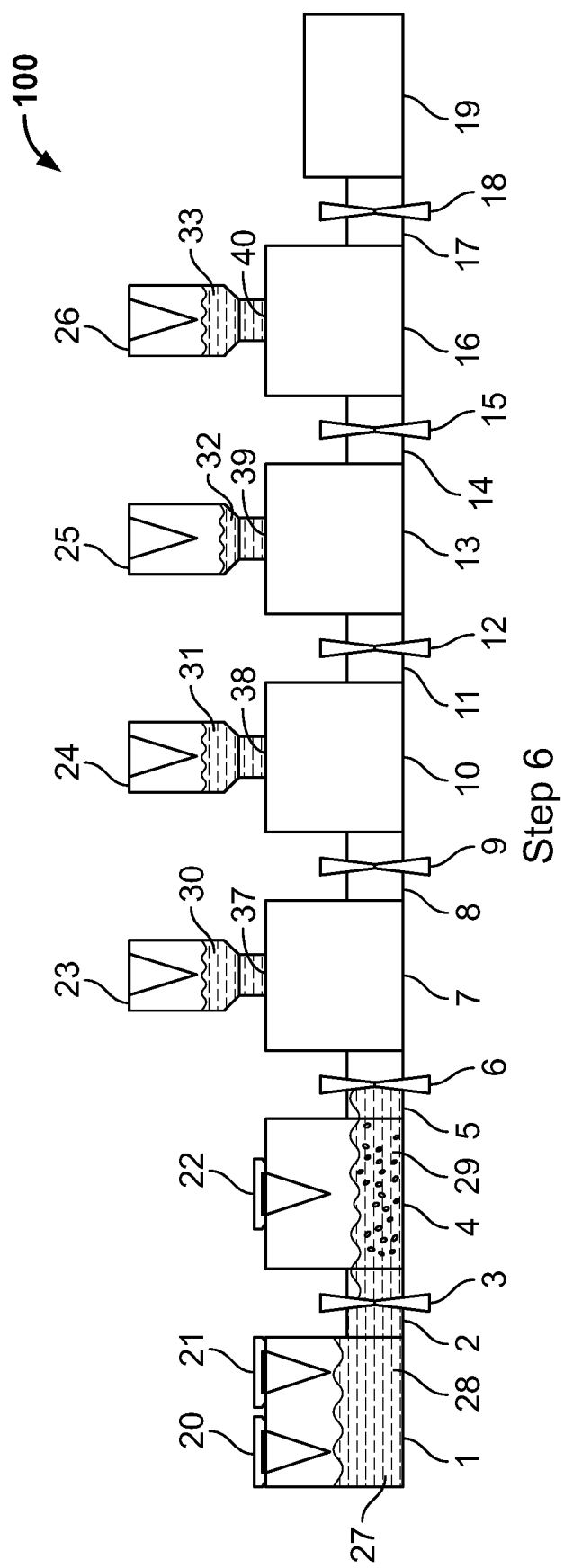
Figure 2:
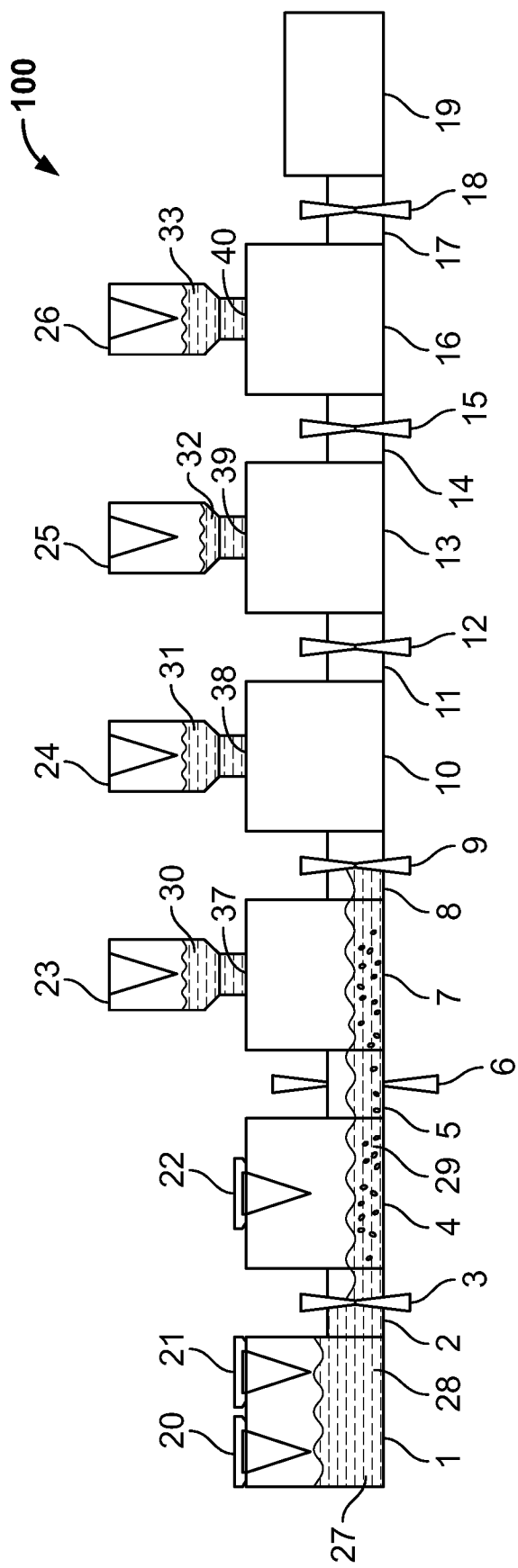
Figure 2:
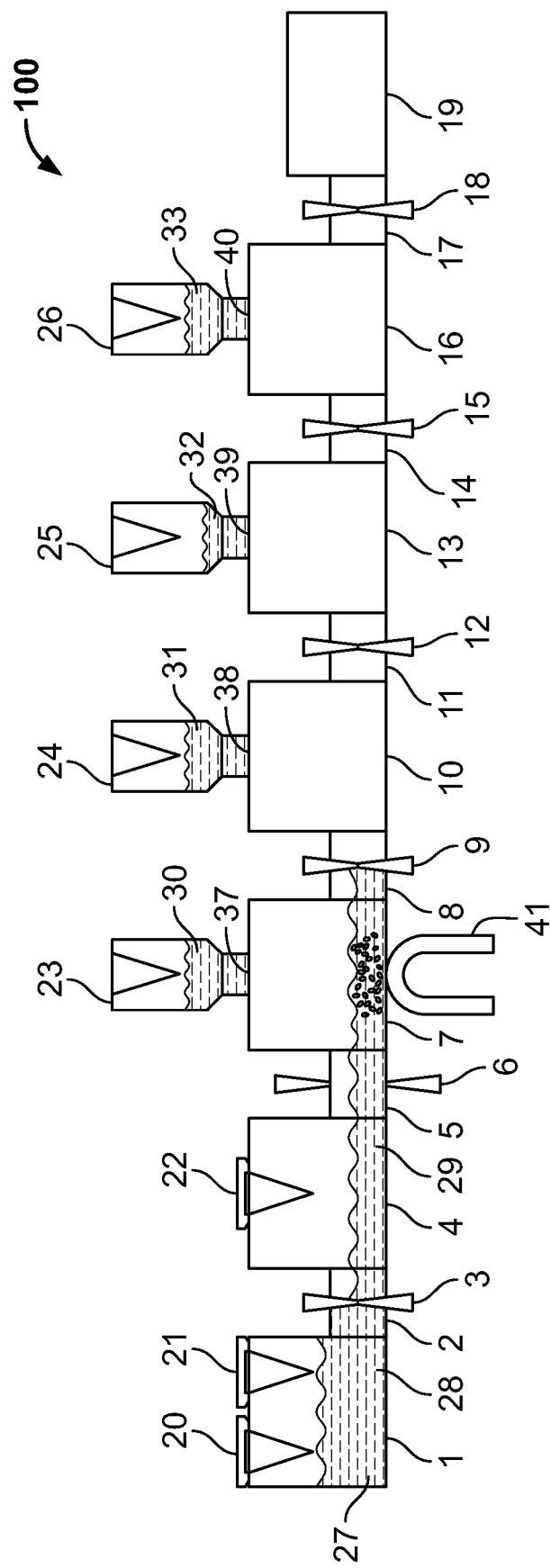
Figure 2:
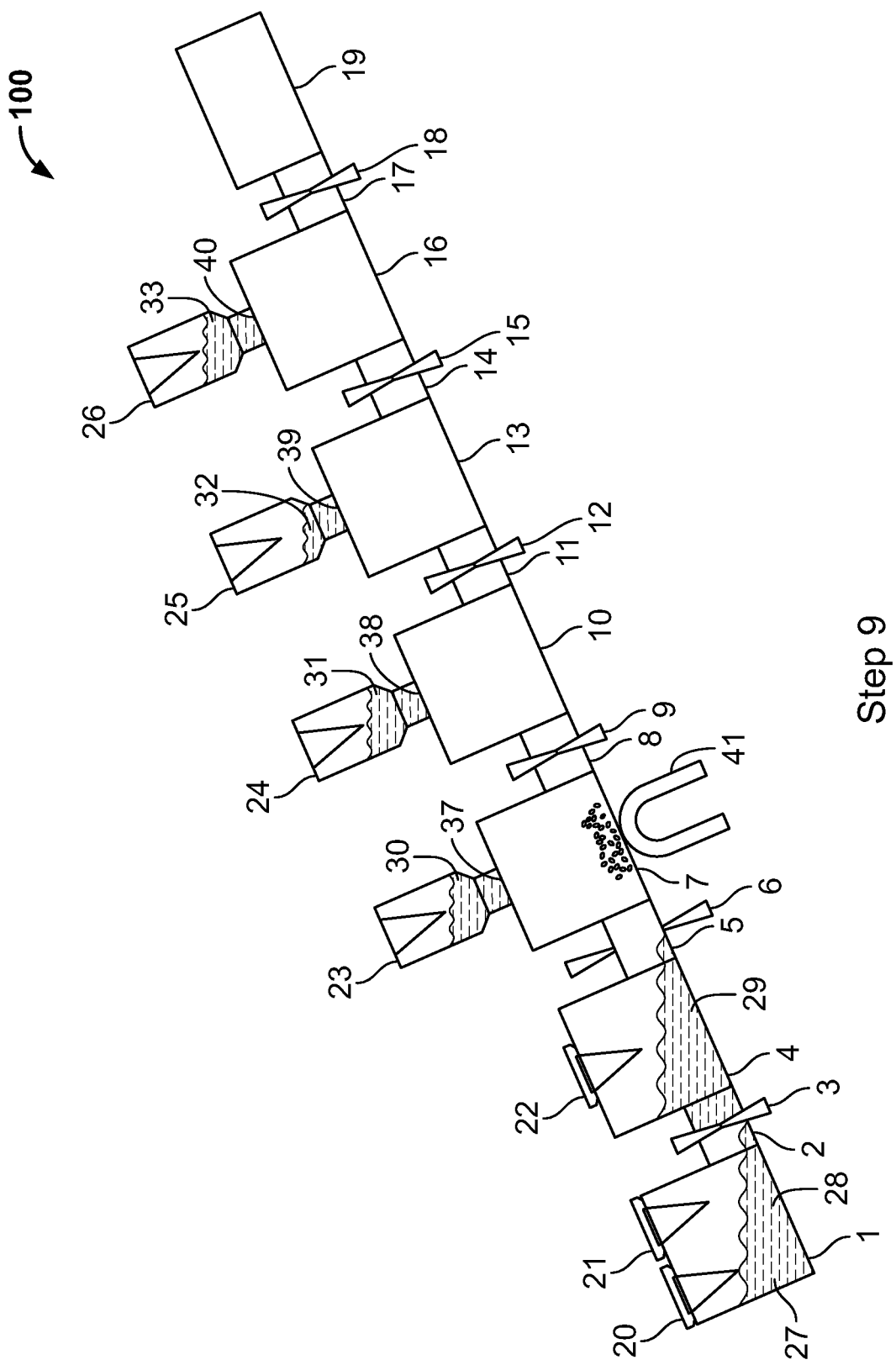
Figure 2:
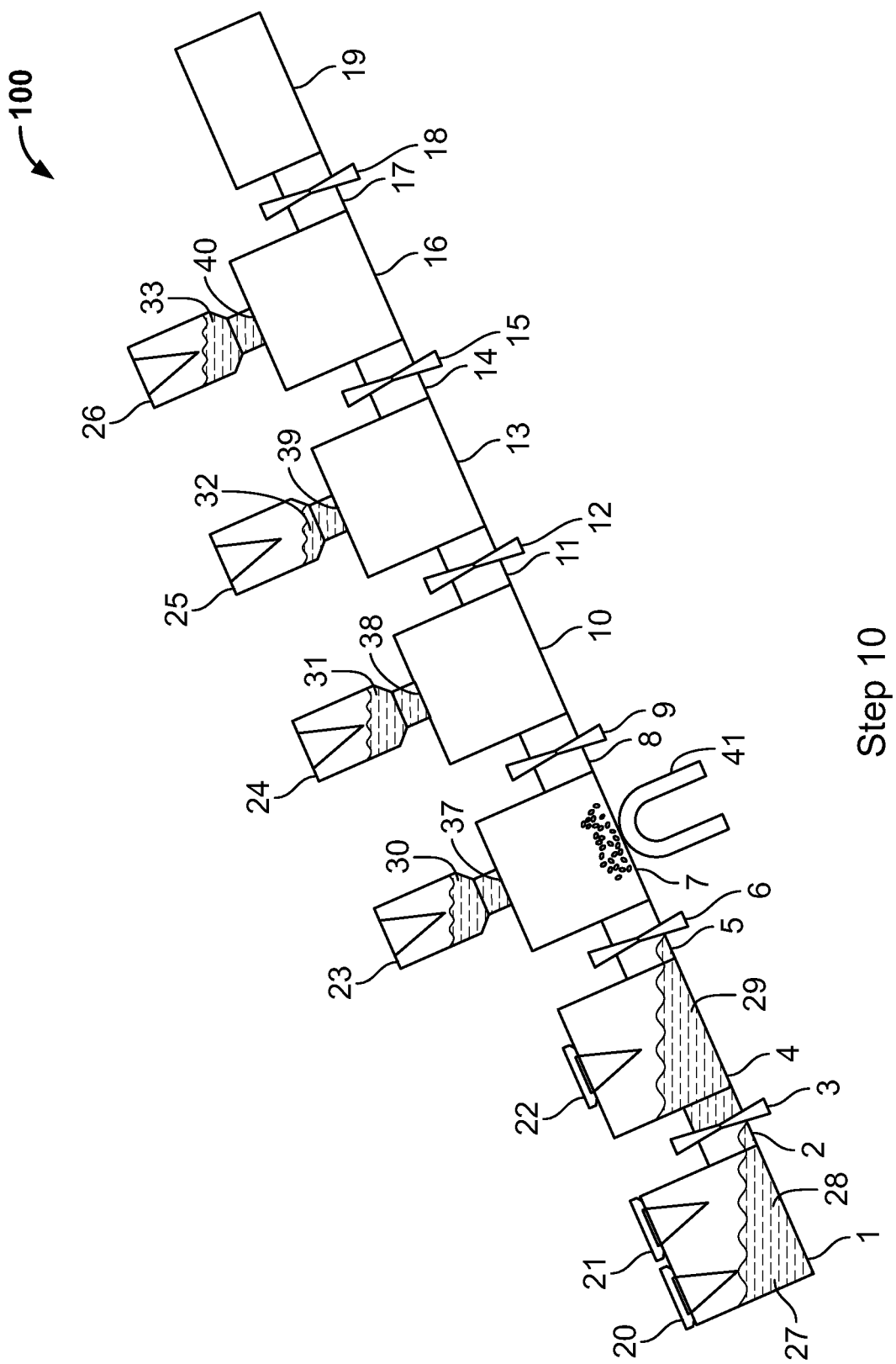
Figure 2:
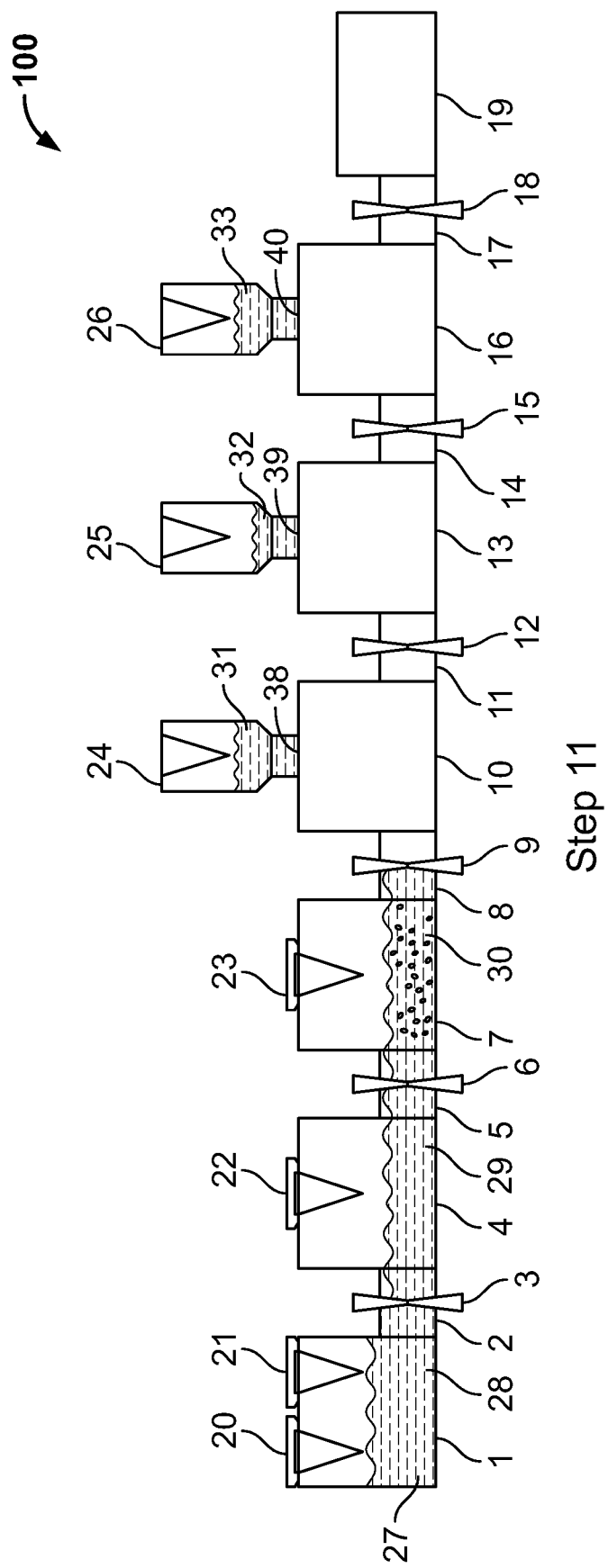
Figure 2:
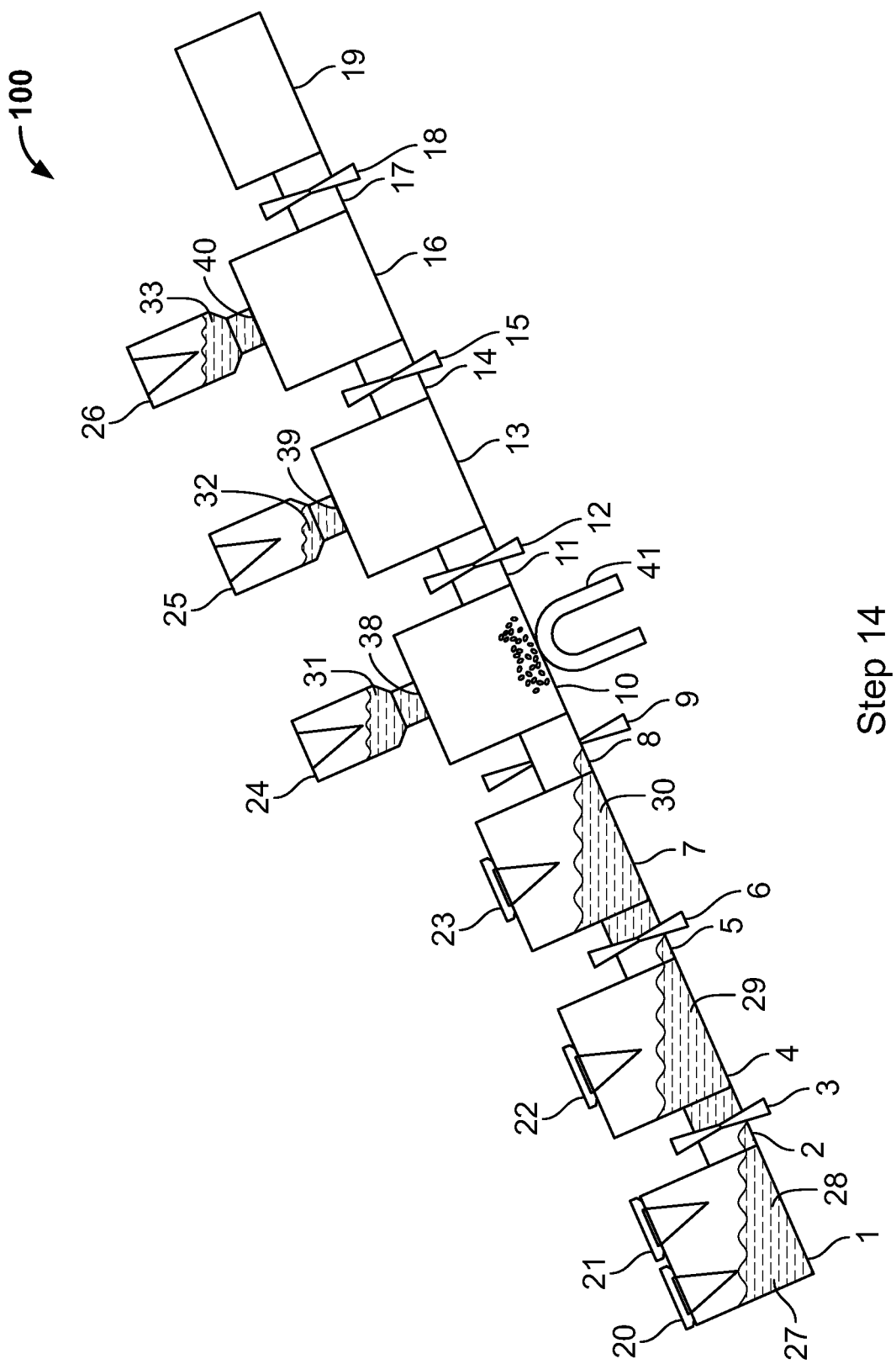
Figure 2:
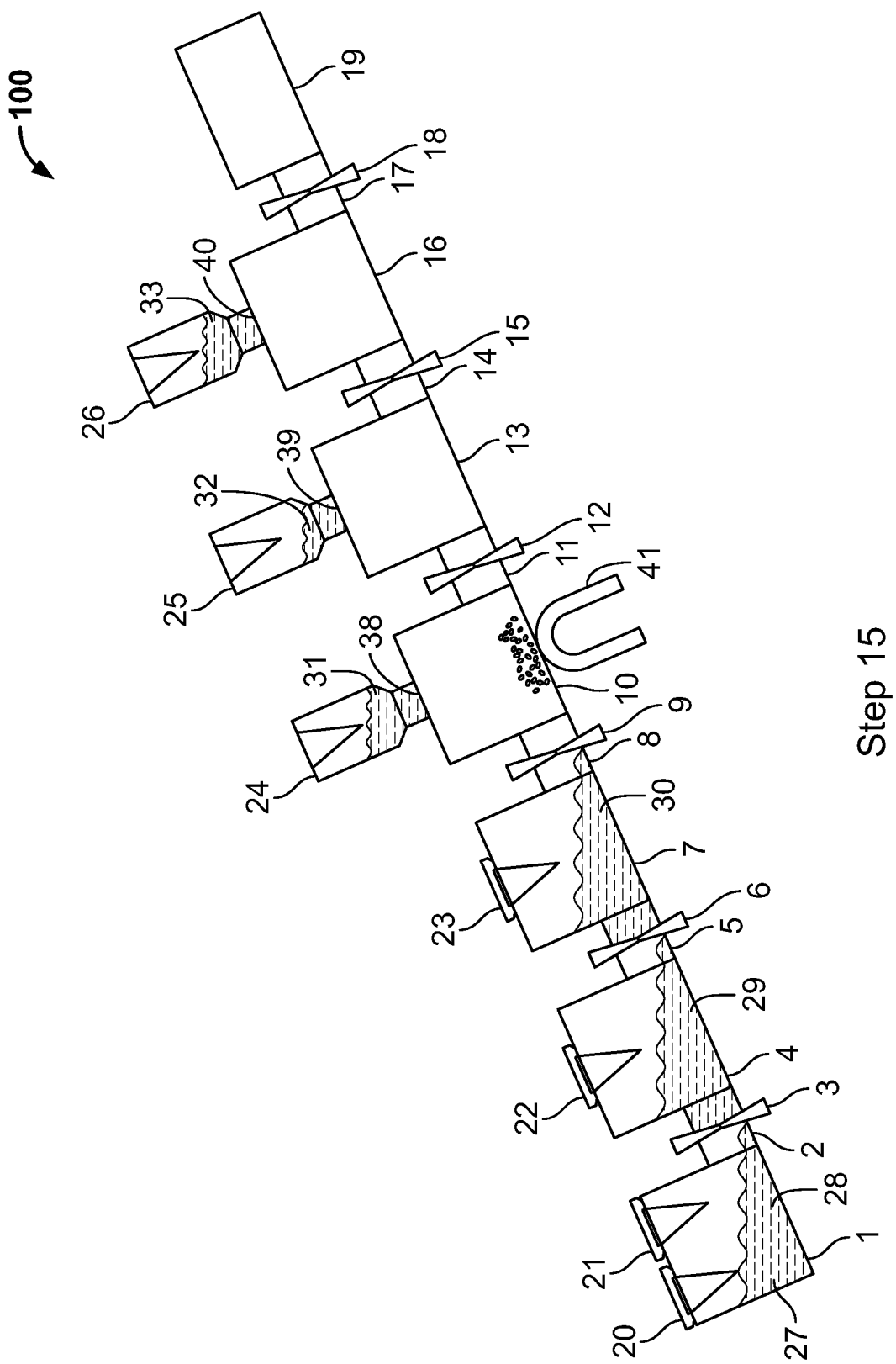
Figure 2:
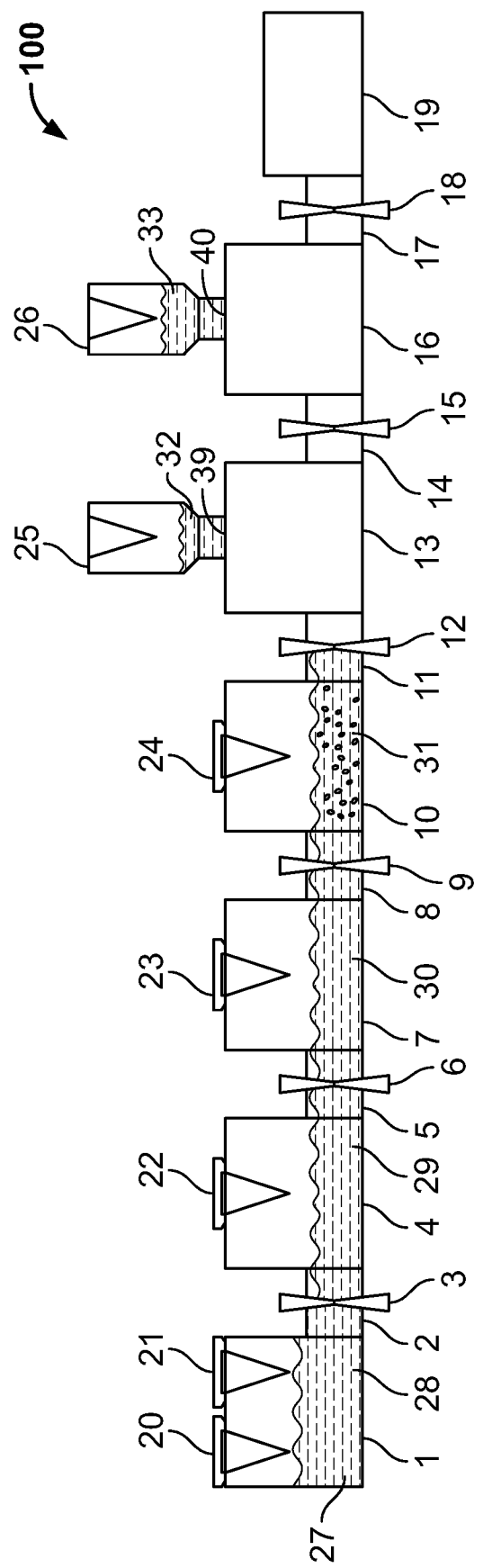
Figure 2:
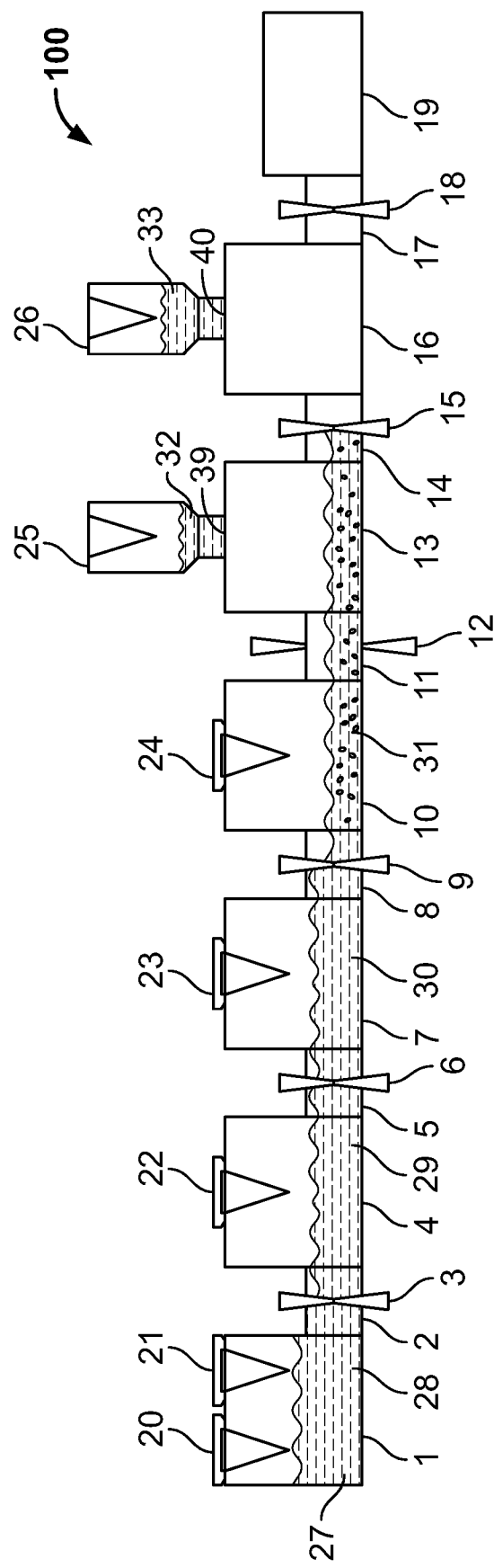
Figure 2:
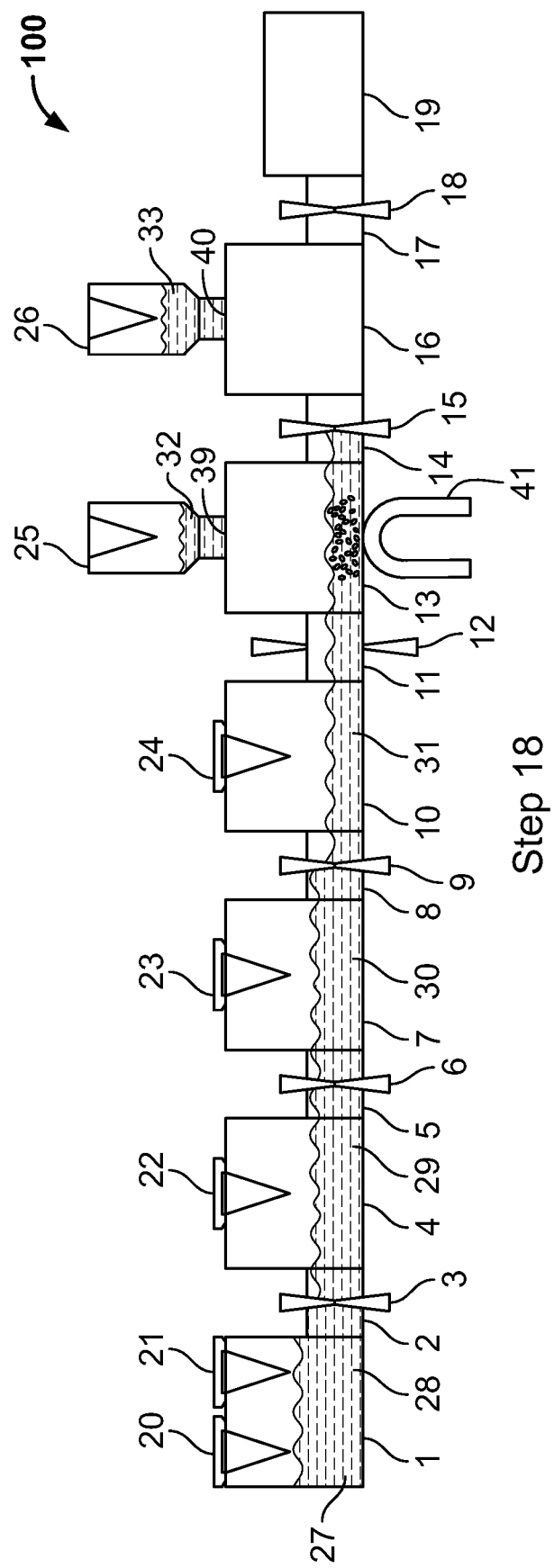
Figure 2:
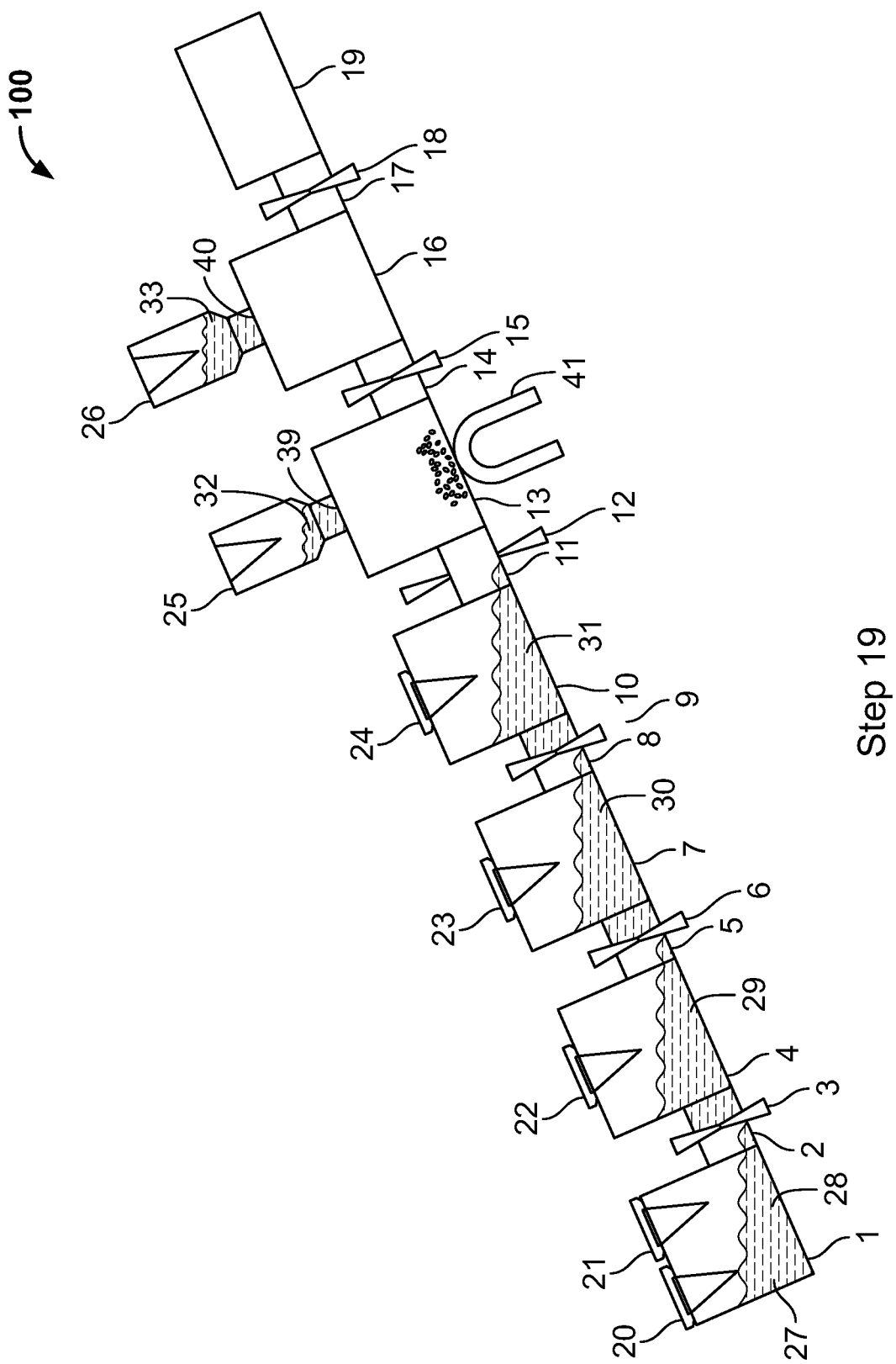
Figure 2:
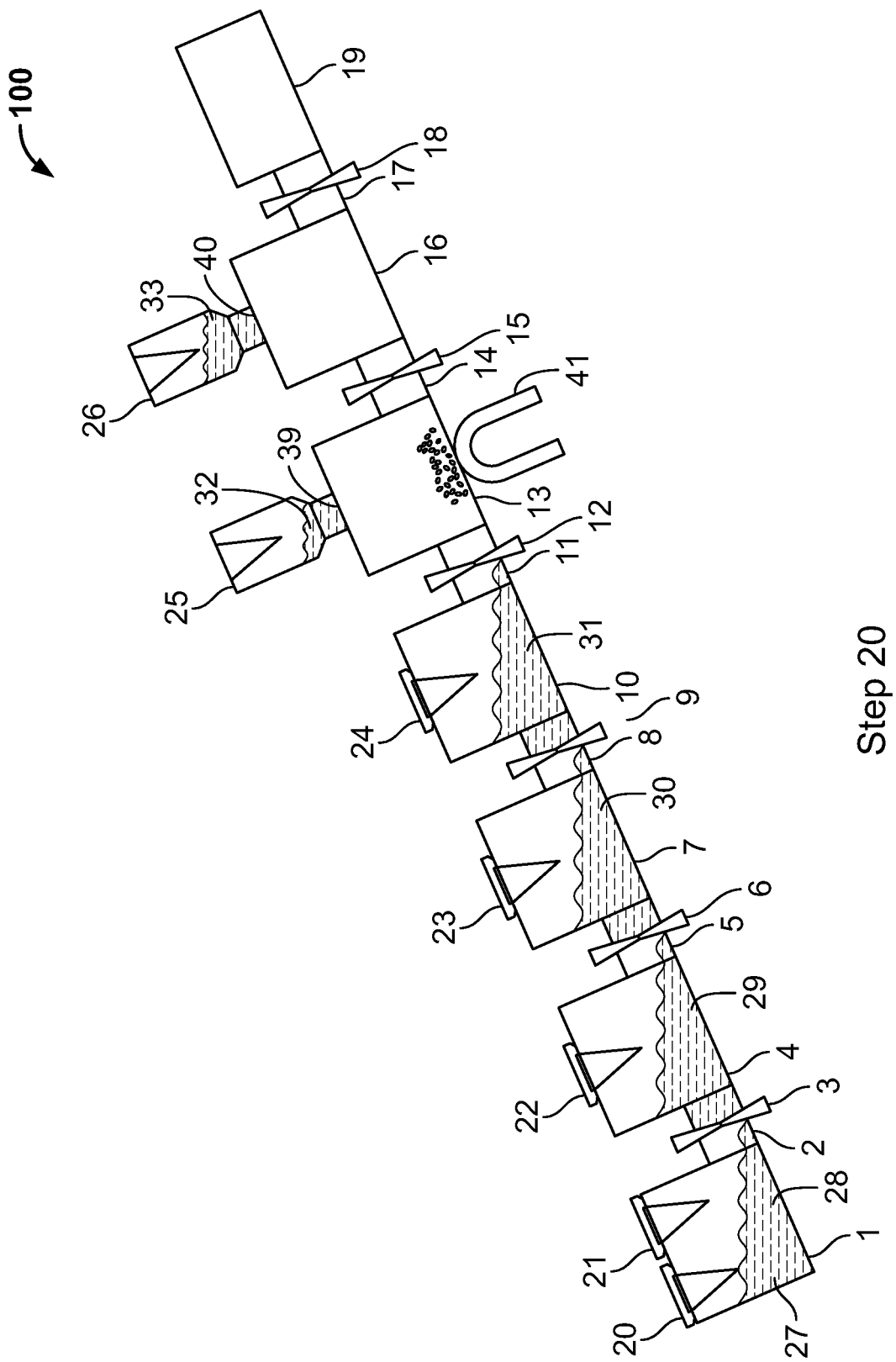
Figure 2:
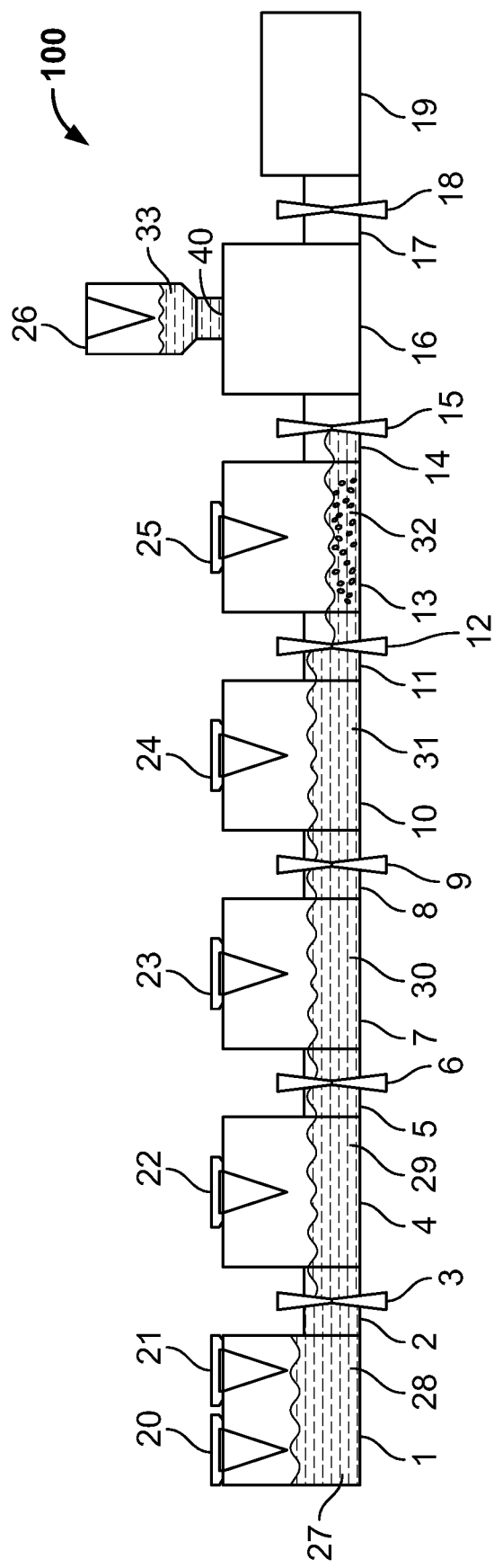
Figure 2:
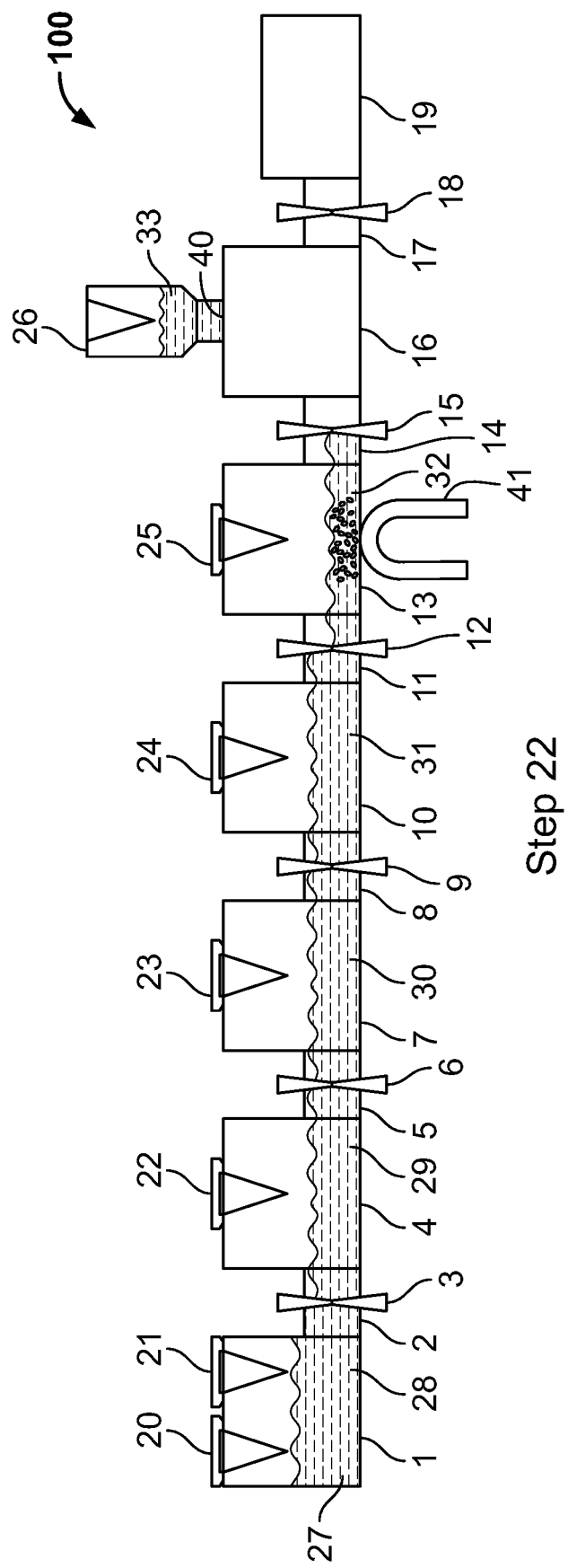
Figure 2:
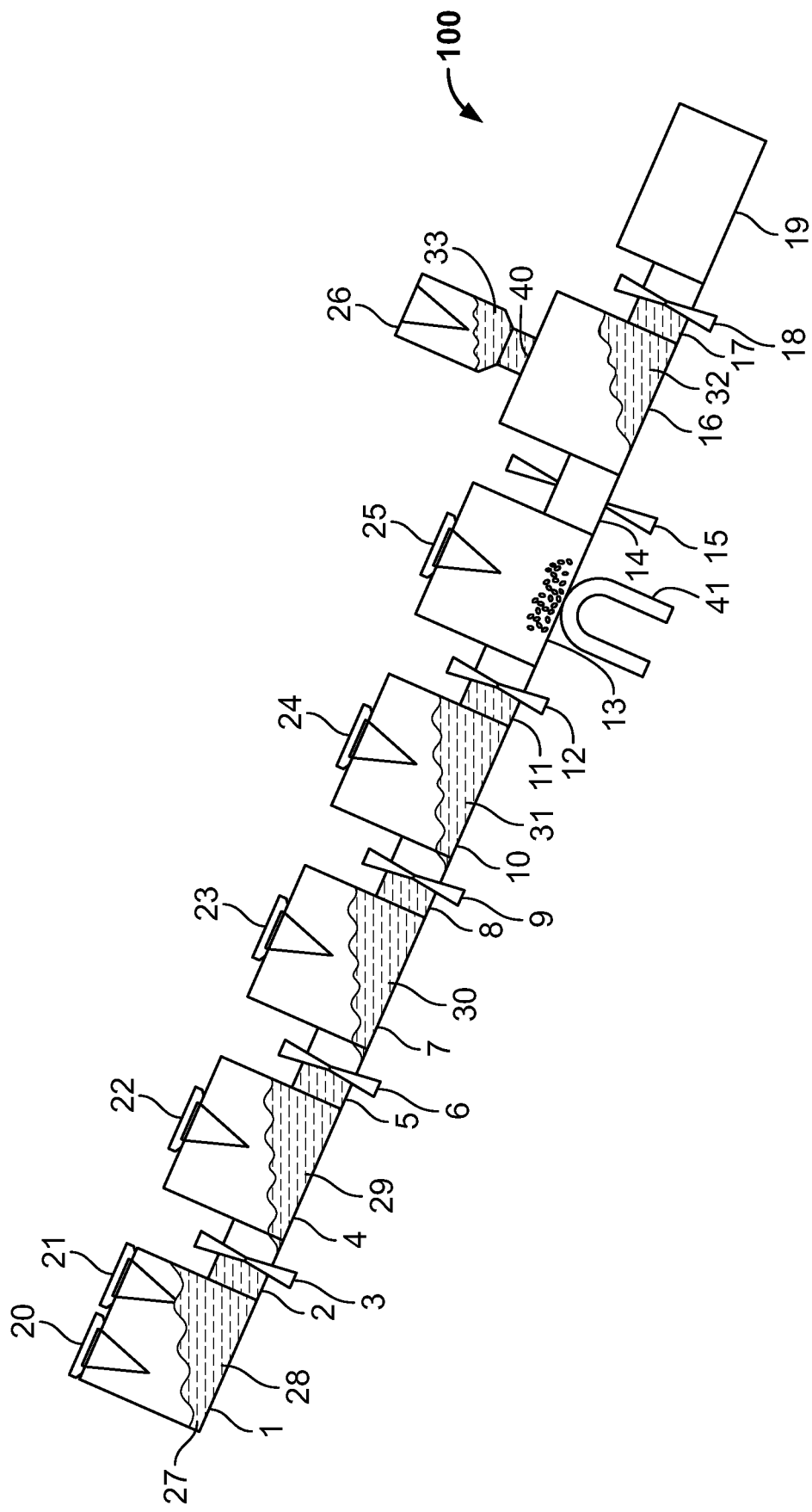
Figure 2:
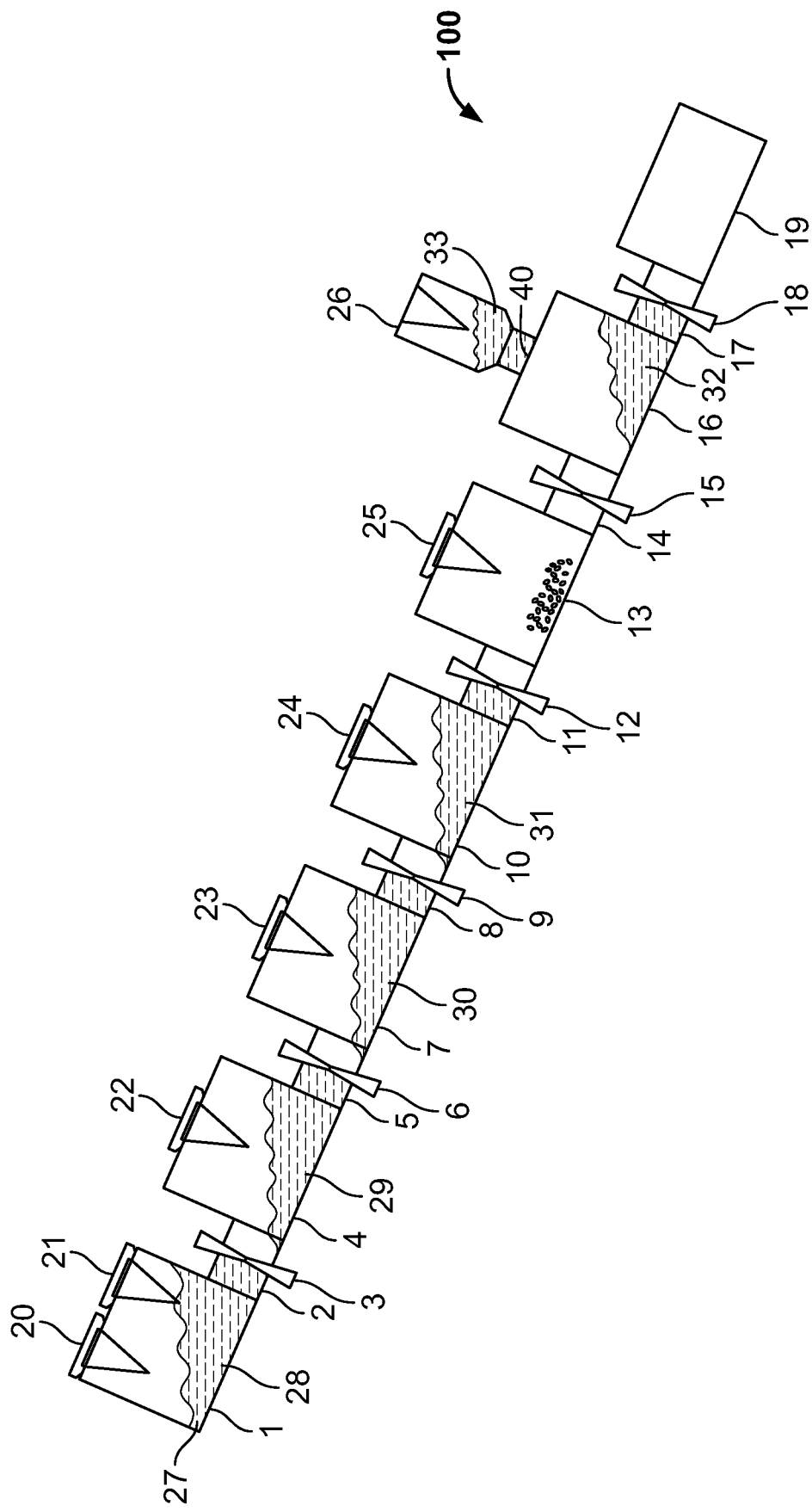
Figure 2:
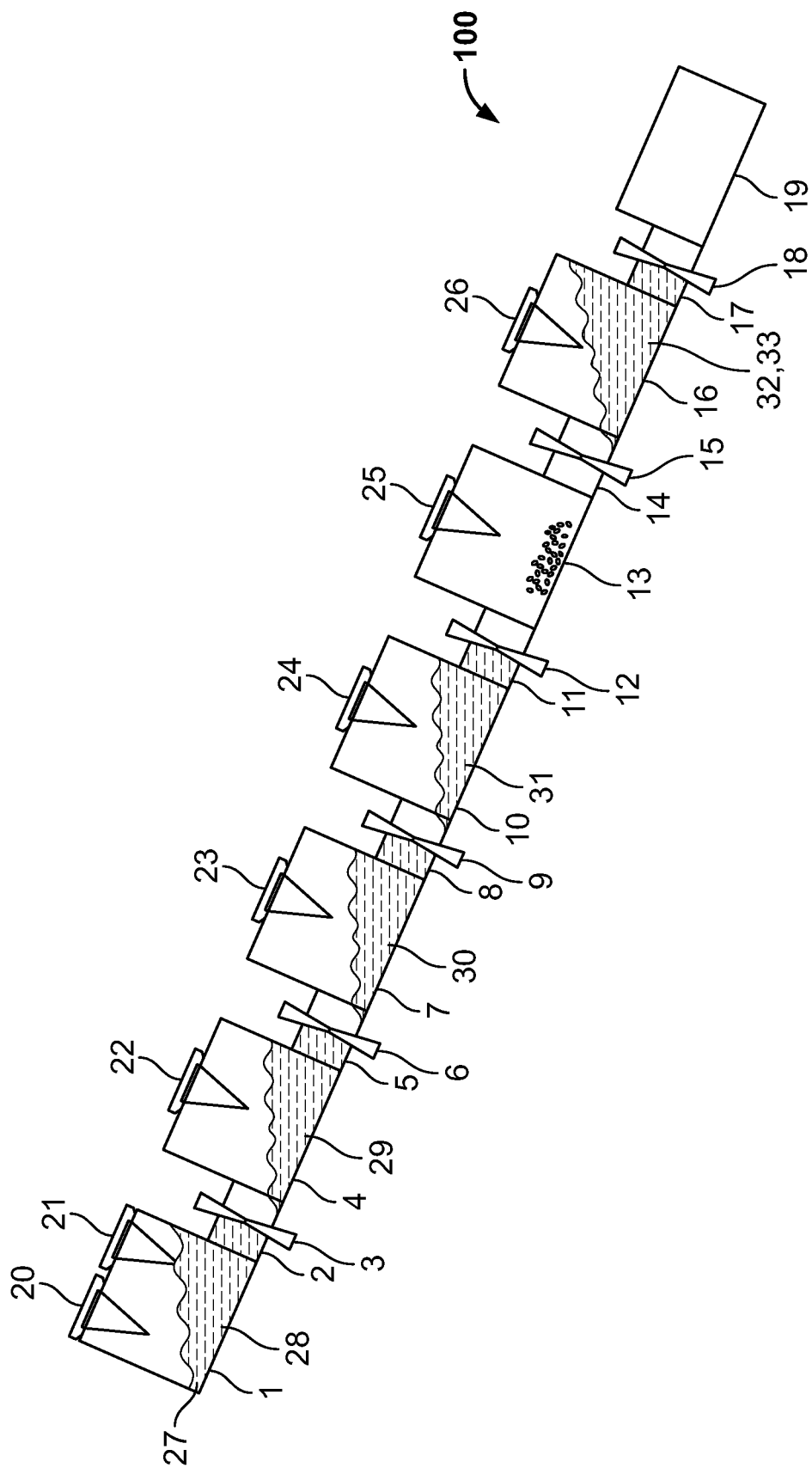
Figure 2:
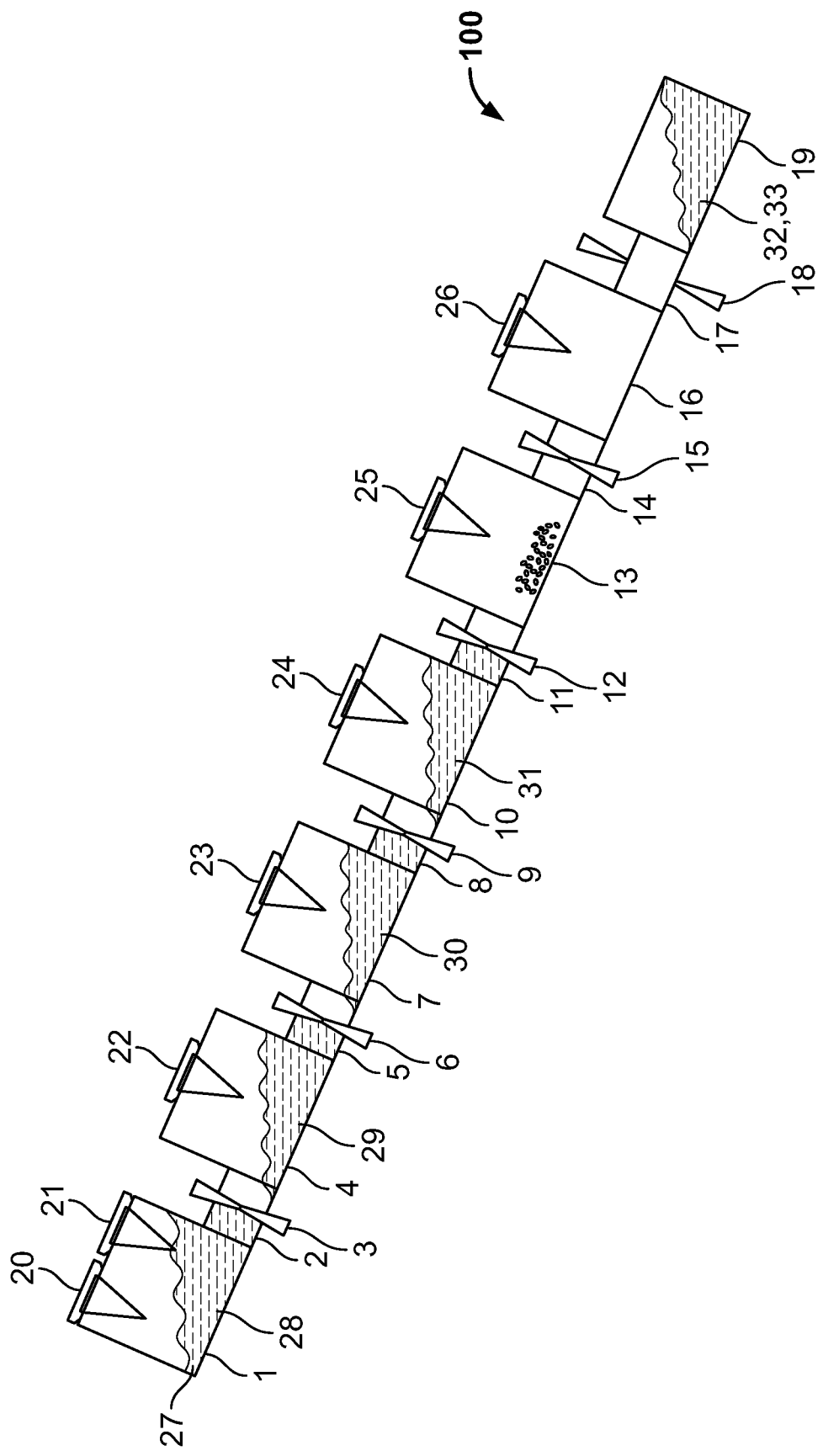
Figure 2:
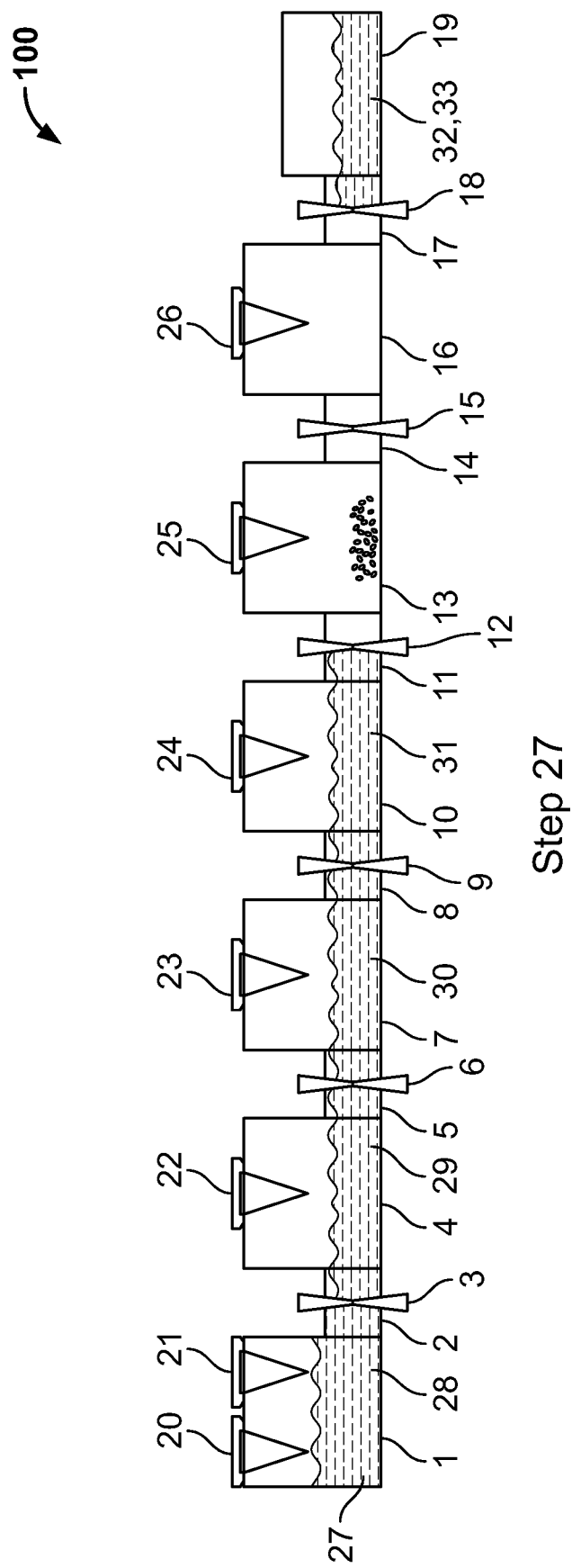

FIG. 2 depicts an exemplary extraction and detection process using the closed extraction and detection component of this disclosure, comprising the following steps (Steps 1-27).

1. Compress storage containers 20 and 21, such that the puncture devices damage the structural integrity of the sealing membrane 34 and 35, thereby allowing the biological sample, magnetic beads, and lysis/binding buffer to be mixed in mixing chamber 1. Sufficient mixing of the biological sample, which is a liquid, solid (optionally in a solution), or solid-liquid suspension, magnetic beads and lysis/binding buffer in the solution is achieved by rotation or vibration, allowing the biomolecules to bind to the magnetic beads. The use of magnetic beads in a magnetic field for purifying biomolecules is well known in the art.

2. Open pressure seal 3, and connect mixing chambers 1 and 4 through connection tube 2.

Prior to opening a pressure seal, the liquid is contained in the mixing chamber 1 and part of the connection tube up until the pressure seal.

3. Magnetic field 41 is placed at mixing chamber 4 to capture and thus enrich for the magnetic beads.

4. Tilt the sealed component, so that the liquid flows into mixing chamber 1. The magnetic beads remain in mixing chamber 4, caught by the magnetic field.

5. Reset the pressure seal 3, close connection tube 2, and stop the liquid flow between mixing chambers 1 and 4.

6. Compress storage container 22, so the puncture device damages the integrity of sealing membrane 36, thereby the magnetic beads and washing solution 29 are allowed to be mixed in mixing chamber 4 and the magnetic beads are washed by rotation or vibration.

7. Open pressure seal 6, and connect mixing chambers 4 and 7 through connection tube 5.

8. Move the magnetic field 41 to mixing chamber 7 to capture and enrich for the magnetic beads.

9. Tilt the sealed component, so that the liquid flows into mixing chamber 4.

10. Reset the pressure seal 6, and close connection tube 5 to stop the liquid flow between mixing chambers 4 and 7.

11-19. Repeat the above steps to wash magnetic beads to remove impurities in mixing chambers 7, 10, and 13, as shown.

20. After washing, the magnetic beads are enriched in mixing chamber 13, and connection tube 12 is closed.

21. Compress storage container 25, so the puncture device damages the structural integrity of sealing membrane 39, thereby the magnetic beads and eluent 32 are mixed and bound materials are eluted from magnetic beads by rotation or vibration.

22. Move the magnetic field 41 to the mixing chamber 13 to capture and enrich for the magnetic beads.

23. Tilt the sealed component, open pressure seal 15, and connect mixing chambers 13 and 16 through connection tube 14, so that the liquid is allowed to flow from mixing chamber 13 into mixing chamber 16.

24. Reset pressure seal 15, and close connection tube 14 to stop the liquid flow between mixing chambers 13 and 16.

25. Compress storage container 26, so the puncture device damages the structural integrity of the sealing membrane 40, thereby allowing the purified sample to be mixed with test solution 33 by rotation or vibration.

26. Open pressure seal 18, and connect mixing chambers 16 and testing chamber 19 through the connection tube 17; then keep the sealed component tilt, so that the liquid flows into the testing chamber 19 for testing by a mounted detection sensor (not shown).

27. Or the testing can be performed by a mounted sensor after the following steps: reset the pressure seal 18 and close the connection tube 17; and the sealed unit can further go back to a specific position.

A person of ordinary skill in the art would appreciate that the above process, or the above process with modifications, can be performed manually, without a machine, or automatically/semi-automatically with the component being placed in a machine or be part of a machine.

FIGS. 1 and 2 provide general description of certain embodiments of this invention. For a specific assay to extract and/or test biomolecules such as small molecules, nucleic acids, and/or proteins, the settings and procedures of the system component can vary, as appropriate for the circumstance, including but not limited to: some mixing chambers may be added, bypassed or omitted; storage containers may contains different reagents specific for individual assays; some storage containers may be empty; and one or more storage containers may be removed or added on some mixing chambers or testing chambers, etc.

Additional modifications of certain embodiments of the component of the component system include, for example: the use of multiple parallel testing chambers/purified sample collection tubes to replace the single testing chamber/purified sample collection tube 19 to perform multiplex testing/sample collection. Multiplex analysis can also be done using multiplex magnetic beads or reagents. One or more detection sensors may be installed to perform the testing in parallel.

In addition, multiple sealed components may be installed in one device to extract and test biomolecules such as small molecules, nucleic acids, and/or proteins from one or more samples in parallel, including but not limited to extracting and testing of DNA and/or RNA in parallel, extracting and testing of DNA, RNA and/or protein in parallel, and the like.

In certain embodiments, the component (i.e., system or unit) can be used for extraction of small molecules/nucleic acids/proteins only without performing testing in order to reserve purified sample for late use. No testing solution is added in this case. After a purified sample is collected in the collection tube 19, the collection tube 19 (i.e., sample collection tube) can be disconnected from the whole unit (i.e. component) and capped for storage.

Any of the buffers and the solutions can be introduced into the storage containers without unsealing the component, such as by injection or by introduced by a pipette through a piercible seal.

For certain test, it may be advantageous to include appropriate standards and/or internal reference.

In certain embodiments, the testing is performed by, for example, immunoassays, nucleic acid detection assays, or biochemical detection. Any appropriate tests are contemplated.

A biomolecule includes any biomolecule, such as, for example, nucleic acids, proteins, and small molecules.

A biological sample includes any biological sample, including, for example, blood, saliva, oral mucosa, body fluids, hair roots, tissues, serum, feces, bodily secretions, medium, and plant.

In certain embodiments, the component further comprises a sample collection device for collecting a biological sample. In certain embodiments, the sample collection device is connected to a storage container or a mixing chamber. In certain embodiments, the sample collection device comprises a puncture device. In certain embodiments, the sample collection device is a micro-sample collection device. In certain embodiments, the sample collection device, such as a device for collecting blood from a patient (e.g., a human patient or an animal), is capped with a sealing cap and the sample collection device is adapted to be screwed onto a mixing chamber, such as, for example, mixing chamber 1, and located on a side of a sealing membrane, such as sealing membrane 34. The sample is not in fluid contact with the mixing chamber 1 at this point. Upon compression, the puncture device damages the structural integrity of the sealing cap and the sealing membrane 34, allowing the biological sample to flow into mixing chamber 1.

In certain embodiments, the sample collection device is a blood collection device. In certain embodiments, the blood collection device is a fingertip lancing device. In certain embodiments, the fingertip lancing device is a fingertip blood collection needle, a swab, absorbent paper, smears, capillary, or a dropper. In certain embodiments, the sample collection device is a scraper for collection of oral mucosa cells or a saliva collector. The blood sample collection device can further comprise an anticoagulant. In certain embodiments, the biological sample is admixed with magnetic beads and with lysis/binding buffer in the sample collection device prior to being added to the component.

In certain embodiments, the component further comprises a trace amount of sample collection. In certain embodiments, the trace amount of sample collection is 10 µl-5 ml of liquid sample. In certain embodiments, the trace amount of sample collection is ≤2 ml, ≤1 ml, ≤0.5 ml, in volume.

The component is adapted for mixing and/or vibration. In certain embodiments, the instrument is adapted for tilting of the closed component of the instrument so that the solution flows in one way from the chamber at the higher position to the chamber at the lower position.

Any suitable testing and analysis known in the art for the purified biomolecules are contemplated. For nucleic acids, the tests and analysis include amplification, sequencing, etc. For proteins and polypeptides, the tests and analysis include size determination, immunoassay, functional analysis such as binding to another molecule, etc. For small molecules, the tests and analysis include spectroscopic analysis, functional analysis such as binding to another molecule, etc.

Figure 3:
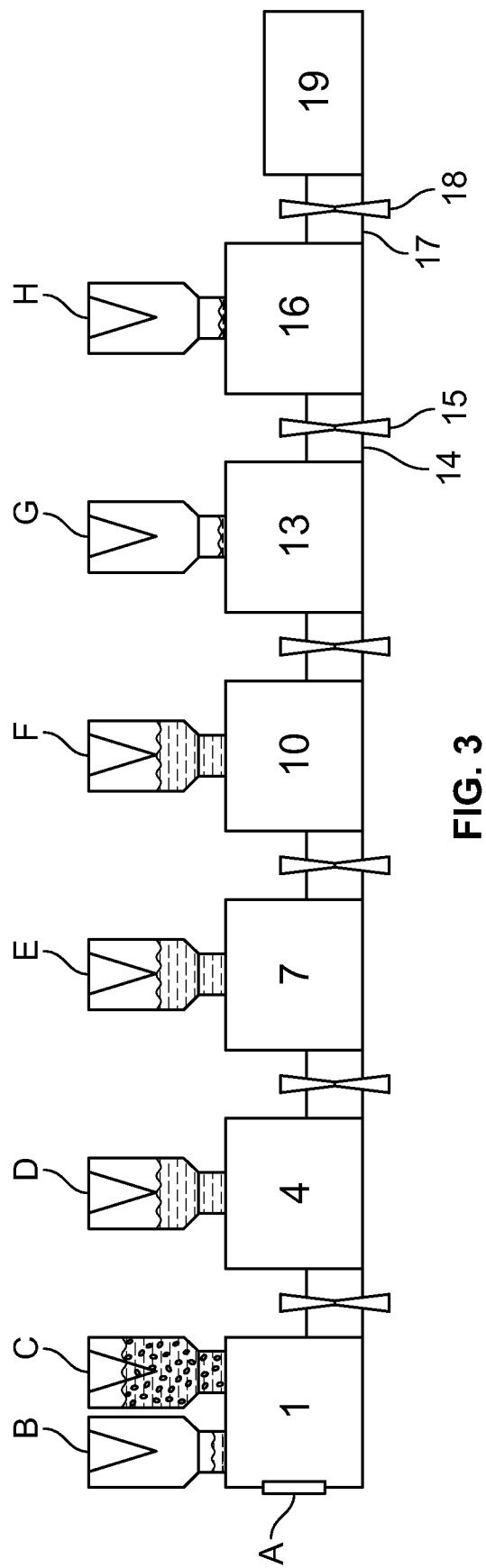
FIG. 3 depicts embodiments of the component of the instrument of this invention for extracting and testing blood DNA, according to embodiments of the present invention.

FIG. 3 depicts embodiments of a component of this invention and of a method of this invention for extracting and testing of blood DNA.

Piercible seal A—blood sample is added through piercible seal A.

Storage container B comprises internal standard 200 µl.

Storage container C comprises magnetic beads and lysis/binding buffer: 1 mg of magnetic beads in 1.5 ml lysis/binding buffer.

Storage container D comprises washing solution I: 1 ml.

Storage container E comprises washing solution II: 1 ml;

Storage container F comprises washing solution III: 1 ml.

Storage container G comprises eluent 100 µl. And storage container H comprises qPCR detection solution 100 µl.

Magnetic beads, lysis/binding buffer, internal standard, washing solution I, washing solution II, washing solution III, eluent, qPCR detection solution (PCR buffer, HBV primer probe, Taq polymerase) are commercially available products (For example: The Emerther Company, Shanghai, China, ThermoFisher Scientific, Waltham, Mass., and Beckman Coulter, Jersey City, N.J.).

After extracting DNA and mixing purified DNA and qPCR detection solution based on the aforementioned procedure (FIG. 2), the nucleic acid solution is transferred to the testing chamber 19 for nucleic acid amplification and detection using a typical amplification assay. A heater/cooler, which can be part of the instrument, or not, is mounted next to the testing chamber 19 to provide suitable temperature for performing qPCR reaction cycles. One or more testing chambers can be used to provide different temperature. A detection sensor such as a photometer is mounted next to the testing chamber 19 to monitor real-time fluorescence emission from the reporter dye. The instrument records the testing result and provides final reading of the quantity of a gene, such as the HBV gene, for medical diagnosis.

Figure 4:
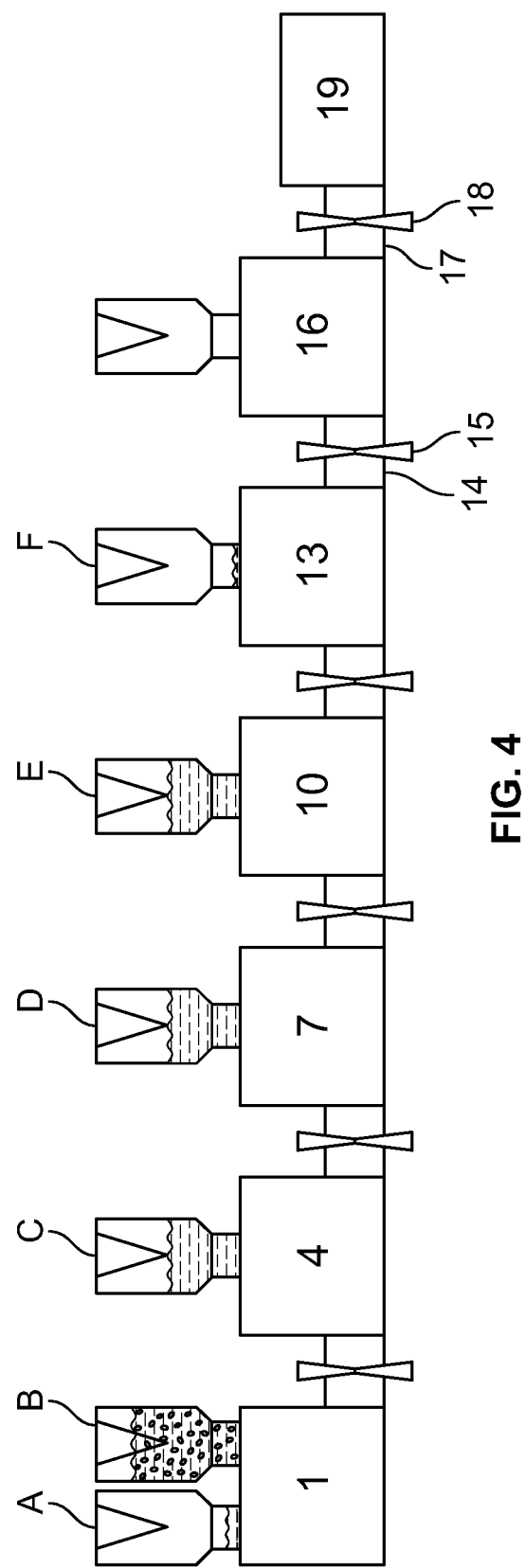
FIG. 4 depicts embodiments of the component of the instrument of this invention for extracting blood DNA, according to embodiments of the present invention.

FIG. 4 depicts embodiments of a component of this invention and of a method of this invention for extracting of blood DNA.

Storage container A comprises biological sample to be purified, 200 µl.

Storage container B comprises magnetic beads and lysis/binding buffer: 1 mg of magnetic beads in 1.5 ml lysis/binding buffer.

Storage container C comprises washing solution I: 1 ml.

Storage container D comprises washing solution II: 1 ml.

Storage container E comprises washing solution III: 1 ml.

And Storage container F comprises eluent 100 µl.

Magnetic beads, lysis/binding buffer, washing solution I, washing solution II, washing solution III, eluent are commercially available products (For example: The Emerther Company, Shanghai, China, ThermoFisher Scientific, Waltham, Mass., and Beckman Coulter, Jersey City, N.J.).

After extraction of DNA based on the aforementioned steps 1-22 (FIG. 2), the sealed unit (i.e., component) is tilted, the pressure seals 15 and 18 are opened, the mixing chambers 13, 16 and the purified sample collection tube 19 are connected through the connection tubes 14 and 17; so that the liquid flows from the mixing chamber 13 through the mixing chamber 16 into the purified sample collection tube 19. The pressure seals 15 and 18 are reset. The connection tubes 14 and 17 are closed. The purified sample is collected in the purified sample collection tube 19 and the purified sample collection tube 19 can be disconnected from the whole unit and caped for storage.

Figure 5:
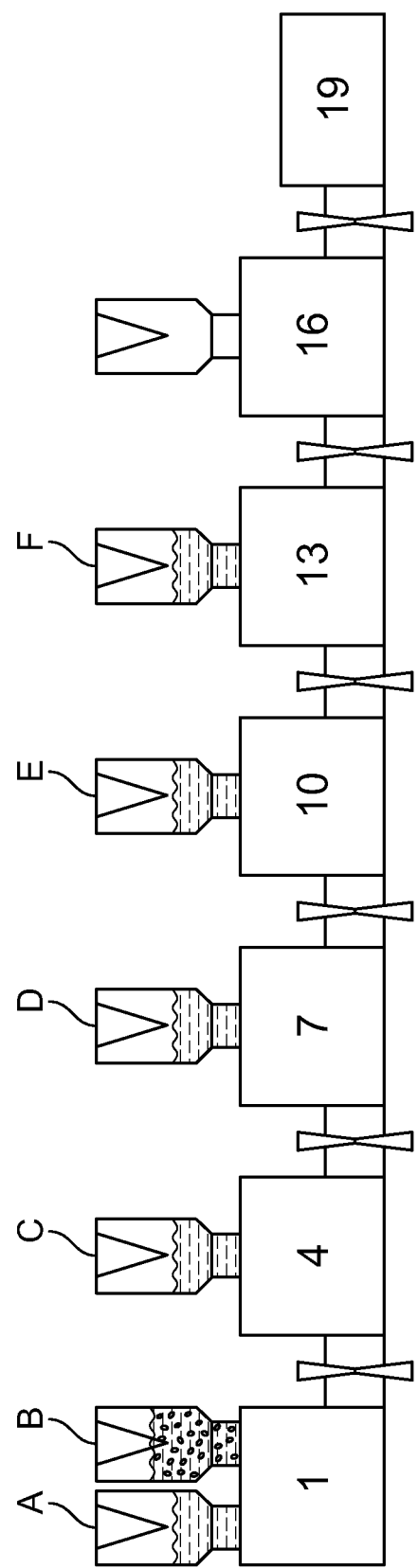
FIG. 5 depicts embodiments of the component of the instrument of this invention for extracting and testing protein using ELISA, according to embodiments of the present invention.

FIG. 5 depicts embodiments of a component of this invention and of a method of this invention for extracting and testing of proteins using ELISA.

Storage container A comprises plasma sample containing an antigen to be analyzed.

Storage container B comprises magnetic beads and binding buffer.

Storage container C comprises washing solution I to remove non-specifically bound proteins.

Storage container D comprises detection antibody solution.

Storage container E comprises washing solution II to remove non-specifically bound proteins.

Storage container F comprises substrate solution.

The detection antibody can be covalently linked to an enzyme, or can itself be detected by a secondary antibody that is linked to an enzyme through bioconjugation. In this example, the detection antibody is covalently linked to an enzyme. The substrate is catalyzed by the enzyme to produce a visible signal, which indicates the quantity of antigen in the sample Magnetic beads, binding buffer, washing solution I, detection antibody solution, washing solution II, substrate solution are commercially available products (For example: The Emerther Company, Shanghai, China, ThermoFisher Scientific, Waltham, Mass., and Beckman Coulter, Jersey City, N.J.).

Plasma sample, magnetic beads and binding buffer are mixed first in the mixing chamber 1 at an appropriate temperature (a heater or a cooler may be mounted in the device). The antigen is bound to magnetic beads. The magnetic beads are moved to the mixing chamber 4 and washed by washing solution I. The magnetic beads are then moved to the mixing chamber 7 and incubated with the detection antibody solution at an appropriate temperature (a heater or a cooler may be mounted in the device). After that, the magnetic beads are moved to the mixing chamber 10 and washed by washing solution II. The magnetic beads are then moved to the mixing chamber 13 and mixed with the substrate solution. The beads and solution are moved to the testing chamber 19 and incubated at an appropriate temperature (a heater or a cooler may be mounted in the device). A detection sensor such as spectrophotometer can be mounted next to the testing chamber 19 to quantify the levels of the antigen.

In certain embodiments, the following component is provided: A fully closed component for purifying a biomolecule from a biological sample, said component comprising: mixing chambers, connection tubes, storage containers, sealing membranes, pressure seals or switches, purified sample collection tubes or testing chambers, a biological sample, in a liquid, solid, or solid-liquid suspension form, magnetic beads, lysis/binding buffer (comprising lysis buffer and/or binding buffer), washing solution, optionally eluent, optionally test solution, and optionally a sample collection device with a sealing cap;
wherein:
each mixing chamber is a disposable plastic container, the mixing chambers being connected to each other by connection tubes, which are sealable soft tubes or switches; each mixing chamber is located adjacently and horizontally or vertically to the next mixing chamber;
pressure seals or switches are adapted for opening and/or closing the connection tubes, to enable or disable the liquid exchange between adjacent mixing chambers, and are located on and around the middle of each connection tube;
one or more of the mixing chambers are connected with one or more storage containers physically but not in liquid contact, with a sealing membrane between the connected mixing chamber and the storage container, said sealing membrane is a piercible membrane, piercible by syringe, pipette, capillary, or by pressure;
the sealing membrane of the storage container prevents the transfer of a biological sample to the mixing chamber before the membrane is pierced;
the storage containers can be stored at different places (for example, locations with different temperature), and attached to mixing chambers or testing chambers prior to operation;
a biological sample, which can be pre-loaded in a sample collection device, which is a compressible plastic container with a sealing cap and a piercing device and which is not part of the component, but can be connected to the component to add the sample; the biological sample can also enter a storage container/a mixing chamber through a sealing membrane or by injection with a syringe or by pipetting; or the biological sample can also be admixed with magnetic beads and lysis/binding solution prior to be added to the component;
when there are more than one storage container mounted on a mixing chamber or a test chamber, they are located next to each other;
each storage container comprises a puncture device;
one or more storage containers comprise washing solution;
one or more storage containers comprise eluent;
one or more storage containers comprise lysis and/or binding buffer; one or more storage containers comprise magnetic beads;
magnetic beads and lysis/binding buffer can be stored in the same or different storage containers;
one or more of the mixing chambers are connected by a connection tube, which is a sealable soft tube or a switch, and a pressure seal on and around the middle of the connection tube, with one or more testing chambers/purified sample collection tubes such that the biological sample isolated from the mixing chamber is transferred to the one or more testing chambers for testing or to the one or more sample collection tubes for collection, One or more storage containers attached to one or more testing chambers or one or more mixing chambers can comprise testing solution or dry powder;
the magnetic beads are brought to contact with the biological sample by rotation or vibration; and
the component is fully closed (i.e., sealed).

In another aspect, a method is provided for purifying a biomolecule from a biological sample, comprising:
 a. Providing a component of this invention, either by itself or housed in an instrument disclosed herein;
 b. Adding a biological sample to the component; and
 c. Purifying a biomolecule using said component.

In further embodiments, the method further comprises testing the purified biomolecules. For example, purified nucleic acid molecules can be sequenced, subjected to PCR amplification, etc.; purified protein molecules can be subjected to any assays, such as immunoassays, etc. In other further embodiments, the method further comprises storing the purified biomolecules. In certain embodiments, other devices may be connected to this machine, such as a computer, a heater/cooler, etc.

Once given the teachings of this disclosure, a person of ordinary skill in the art can modify the method of this aspect to suit each application.

In another aspect, a method is provided for purifying a biomolecule from a biological sample, comprising:

(a) Providing a magnetic field and a component of this invention, either by itself or housed in an instrument disclosed herein;
(b) Introducing a biological sample to the component, by, for example, placing the biological sample in a first storage container; compressing the first storage container such that the puncture device damage the structural integrity of the sealing membrane, thereby allowing the biological sample, magnetic beads, and lysis/binding buffer to be mixed in the connected mixing chamber (first mixing chamber), which is the leftmost or the rightmost chamber of the component (a chamber is either a mixing chamber or a test chamber), wherein the magnetic beads and/or lysis/binding buffer, which can be either a binding buffer or a lysis buffer, or both, are introduced into the first mixing chamber either from the first storage container with the sample or another storage container in physical contact with the first mixing chamber and upon compressing that storage container, the puncture device damage the structural integrity of the sealing membrane, allowing the magnetic beads and lysis/binding buffer to enter into the first mixing chamber; wherein the biological sample can be introduced into the component by other manner, as disclosed herein, and the magnetic beads and lysis/binding buffer can be placed in the same storage containers or be separated in different storage containers;
(c) mixing the biological sample, magnetic beads and lysis/binding buffer in the solution by rotation or vibration;
(d) opening pressure seal (first pressure seal) between the first and an adjacent mixing chamber (second mixing chamber) thereby connecting the two mixing chambers through the connection tube in between them (first connection tube); wherein, depending on the application, there can be more or less pressure seals; more or less mixing chambers, and more or less connection tubes;
(e) placing the magnetic field below the second mixing chamber comprising the sample and the solution to capture and thus enrich for the magnetic beads;
(f) tilting the sealed component, so that the liquid flows into the first mixing chamber; the magnetic beads remaining in the second mixing chamber due to the magnetic field;
(g) Closing the first pressure seal, thus closing the first connection tube, and stopping the liquid flow between the first and the second mixing chambers;
(h) Compressing a storage container (the second storage container) connected to the second mixing chamber, so the puncture device damages the integrity of sealing membrane, thereby introducing the washing solution in the second storage container (the second storage container comprises a washing solution) into the second mixing chamber such that the magnetic beads and washing solution are allowed to be mixed in the second mixing chamber and the magnetic beads are washed by rotation or vibration;
(i) Opening a pressure seal between the second mixing chamber and an adjacent mixing chamber (third mixing chamber) that is not the first mixing chamber, and connecting the second and third mixing chambers through a connection tube between them (second connection tube);
(j) Moving the magnetic field to below the third mixing chamber to capture and enrich for the magnetic beads;
(k) Tilting the sealed component, so that the liquid flows into the second mixing chamber;
(l) Resetting the second pressure seal, and closing the second connection tube to stop the liquid flow between the second and third mixing chambers;

(m) Optionally repeating washing steps (d)-(l) to remove impurities in additional mixing chamber(s) adjacent to the third mixing chamber but distal to the second mixing chamber;
(n) After washing, the magnetic beads are enriched in the second to last mixing chamber in which the final washing was performed and closing the connection tube between this mixing chamber and the one adjacent to it (third to last mixing chamber) from which the magnetic beads resided prior to residing in the second to last mixing chamber, the second to last mixing chamber is more distal to the first mixing chamber than the third to last mixing chamber;
(o) Compressing a storage container above the second to last mixing chamber (second to last storage container), which container comprises the eluent, so the puncture device damages the structural integrity of sealing membrane, thereby the magnetic beads and eluent are mixed and the bound materials on the magnetic beads are eluted from magnetic beads by rotation or vibration;
(p) Moving the magnetic field to the second to last mixing chamber to capture and enrich for the magnetic beads;
(q) Tilting the sealed component, opening pressure seal (second to last pressure seal) between the second to last mixing chamber and the last mixing chamber, and connecting the second to last mixing chamber and the last mixing chamber with the opened connection tube between these two mixing chambers (second to last connecting tube), so that the liquid is allowed to flow from the second to last mixing chamber into the last mixing chamber;
(r) Resetting the second to last pressure seal, and closing the second to last connection tube to stop the liquid flow between the second to last mixing chamber and the last mixing chamber;
(s) Compressing a storage container (last storage container) comprising a test solution/dry powder connected to the last mixing chamber, so the puncture device damages the structural integrity of sealing membrane, thereby allowing the purified sample to be mixed with test solution/dry powder by rotation or vibration;
(t) Opening pressure seal (last pressure seal), and connecting the last mixing chamber and testing chamber through the last connection tube, the test chamber being the most distal chamber from the first mixing chamber, then keep the sealed component tilt, so that the liquid flows into the testing chamber for testing.
(u) The purified sample can also be collected in a purified sample collection tube for storage after biomolecules are eluted from magnetic beads (step p), without the addition of test solution/dry powder or testing;
(v) For some specific assays, some aforementioned steps may be omitted, such as no elution step or testing step; some more steps may be added, such as addition of enzymes, antibody solution, substrate solution and/or additional incubations.

In certain embodiments, the method of this aspect further comprises testing by a mounted detection sensor on the component; or the testing can be performed by a mounted sensor after the following steps: resetting the last pressure seal and closing the last connection tube. The detection sensor can be part of the instrument, part of the component, or neither. Once given the teachings of this disclosure, a person of ordinary skill in the art can modify the method of this aspect to suit each application. For example, there can be more or less mixing chambers, more or less connection tubes, more or less storage containers, more or less sealing membranes, more or less pressure seals or switches, and more or less purified sample collection tubes or testing chambers. There can be one or more washing set of steps, one or more sample collection devices disclosed herein. In some cases, some mixing chambers may be added, bypassed or omitted; storage containers may contains different reagents specific for individual assays; some storage containers may be empty; and one or more storage containers may be removed or added on some mixing chambers or testing chambers, etc. Additional modifications include, for example: the use of multiple parallel testing chambers/purified sample collection tubes to replace the single testing chamber/purified sample collection tube to perform multiplex testing/sample collection. Multiplex analysis can also be done using multiplex magnetic beads or reagents. One or more detection sensors may be installed to perform the testing in parallel. In addition, multiple sealed components may be installed in one device to extract and test biomolecules such as small molecules, nucleic acids, and/or proteins from one or more samples in parallel, including but not limited to extracting and testing of DNA and/or RNA in parallel, extracting and testing of DNA, RNA and/or protein in parallel, and the like. There can be more or less numbers of mixing chambers, connection tubes, storage containers, sealing membranes, pressure seals or switches, and purified sample collection tubes or testing chambers, more biological samples; more magnetic beads, lysis/binding buffer, washing solution, optionally eluent, and optionally test solution can be added, optionally a sample collection device with a sealing cap can be added, optionally a heater and/or cooler can be added, and optionally a detection sensor can be added.

As used herein, the word "a" or "plurality" before a noun represents one or more of the particular noun.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting.

All publications, patent applications, patents, sequences, database entries, and other references mentioned herein are incorporated by reference in their entirety. In case of conflict, the present specification, including definitions, will control.

The foregoing description discloses only exemplary embodiments of the invention. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

We claim:

1. A fully-closed component for purifying a biomolecule from a biological sample, said component comprising: a plurality of mixing chambers; a plurality of connection tubes; a plurality of storage containers; a plurality of pierceable sealing membranes; a plurality of pressure seals or switches; purified sample collection tubes or testing chambers; magnetic beads; lysis buffer and/or binding buffer; washing solution; and optionally eluent;

wherein:
each mixing chamber is a plastic container, the mixing chambers being connected to each other by connection tubes, which are switches or sealable tubes; each mixing chamber is located adjacently and horizontally or adjacently and vertically to the next mixing chamber;
the pressure seals or switches are adapted for opening and/or closing the connection tubes, to enable or disable liquid exchange between adjacent mixing chambers, and are located on and around the middle of each connection tube;
one or more of the mixing chambers are connected with one or more storage containers physically but not in liquid contact, with a pierceable sealing membrane between the connected mixing chamber and the storage container, each said storage container is located above or below the mixing chamber the storage container is connected to;
the pierceable sealing membrane of a storage container is adapted to prevent the transfer of a liquid, solid, or solid-liquid suspension in the storage container to the mixing chamber before the membrane is pierced;
when there is more than one storage container mounted on a mixing chamber or a testing chamber, they are located next to each other;
each storage container comprises a puncture device;
one or more storage containers comprise washing solution;
one or more storage containers optionally comprise eluent;
one or more storage containers comprise lysis buffer and/or binding buffer;
one or more storage containers comprise magnetic beads;
one or more mixing chambers are connected to one or more testing chambers or purified sample collection tubes, located above, below or adjacent to said one or more mixing chambers, each of said one or more mixing chambers is connected to each of said one or more testing chambers or purified sample collection tubes by a connection tube;
one or more of said plurality of storage containers are attached to one or more of said plurality of testing chambers or one or more of said plurality of mixing chambers optionally comprising solution or dry powder; and
the component is fully closed.

2. The component of claim 1, wherein the component is part of a machine.

3. The component of claim 1, wherein the pierceable sealing membrane of a storage container is a sealed foil, plastic or rubber closure.

4. The component of claim 1, wherein one or more of the storage containers is mounted above a mixing chamber or a testing chamber.

5. The component of claim 1, wherein different sets of magnetic beads and lysis buffer and/or binding buffer are placed in different storage containers, each set having a different adsorption and binding profile such that each different set is for adsorption and binding of small molecules, proteins or nucleic acids.

6. The component of claim 1, further comprising one or more detection sensors.

7. An instrument comprising the component of claim 1, a moving magnetic field generator capable of generating a moving magnetic field, a motor, and optionally a detection sensor, wherein said component in said instrument is adapted to rotate, vibrate, or tilt and wherein the instrument is adapted to be powered by a power supply.

8. A method for purifying a biomolecule from a biological sample, comprising:
 (a) providing the component of claim 1, either by itself or housed in a machine;
 (b) adding a biological sample into said component; and
 (c) purifying a biomolecule using said component.

9. The method of claim 8, further comprising (d) conducting testing on said biomolecule using said component.

10. The method of claim 8, wherein the component is housed inside a machine.

11. The method of claim 8, further comprising storing said biomolecule in said component.

* * * * *